United States Patent
Kim et al.

(10) Patent No.: US 11,583,689 B2
(45) Date of Patent: Feb. 21, 2023

(54) COMPOSITION FOR ATOPY OR PSORIASIS TREATMENT COMPRISING LIQUID TYPE PLASMA

(71) Applicant: AJOU UNIVERSITY INDUSTRY-ACADEMIC COOPERATION FOUNDATION, Suwon-si (KR)

(72) Inventors: Chul Ho Kim, Seoul (KR); Yun Sang Lee, Seoul (KR); Myeong Hoon Lee, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 992 days.

(21) Appl. No.: 16/335,904

(22) PCT Filed: Sep. 19, 2017

(86) PCT No.: PCT/KR2017/010235
§ 371 (c)(1),
(2) Date: Mar. 22, 2019

(87) PCT Pub. No.: WO2018/056665
PCT Pub. Date: Mar. 29, 2018

(65) Prior Publication Data
US 2020/0179709 A1    Jun. 11, 2020

(30) Foreign Application Priority Data

Sep. 22, 2016 (KR) .................. 10-2016-0121358
Sep. 22, 2016 (KR) .................. 10-2016-0121359
(Continued)

(51) Int. Cl.
*A61N 1/44* (2006.01)
*H01J 37/32* (2006.01)

(52) U.S. Cl.
CPC .......... *A61N 1/44* (2013.01); *H01J 37/32082* (2013.01); *H01J 37/32825* (2013.01); *H01J 2237/33* (2013.01)

(58) Field of Classification Search
None
See application file for complete search history.

(56) References Cited

U.S. PATENT DOCUMENTS 1,546,476 A * 7/1925 Crockett .................. D01H 1/20
74/606 R
3,951,218 A * 4/1976 Sjogren ................. E21B 43/117
175/4.6
(Continued)

FOREIGN PATENT DOCUMENTS

JP  2015084290  4/2015
KR  20080004452  1/2008
(Continued)

OTHER PUBLICATIONS

Abbas et al., Cellular and Molecular Immunology, pp. 456, Table 19-4.
(Continued)

*Primary Examiner* — Srinivas Sathiraju
(74) *Attorney, Agent, or Firm* — Cantor Colburn LLP

(57) ABSTRACT

The present invention relates to a composition for atopy or psoriasis treatment comprising a plasma-treated liquid material. More particularly, the present invention relates to a method for producing a plasma-treated liquid material for preventing or treating atopic dermatitis or psoriasis, a pharmaceutical composition for preventing or treating a topic dermatitis or psoriasis using a plasma-treated liquid material produced according to the method, and a method for pre-
(Continued)

venting or treating atopic dermatitis or psoriasis using the plasma-treated liquid material.

16 Claims, 18 Drawing Sheets

Specification includes a Sequence Listing.

(30) Foreign Application Priority Data

Aug. 8, 2017 (KR) .................. 10-2017-0100290
Aug. 8, 2017 (KR) .................. 10-2017-0100291

(56) References Cited

U.S. PATENT DOCUMENTS

| | | | | |
|---|---|---|---|---|
| 4,974,487 | A * | 12/1990 | Goldstein | F41B 6/00 219/121.36 |
| 5,586,981 | A * | 12/1996 | Hu | A61B 18/203 606/9 |
| 5,782,249 | A * | 7/1998 | Weber | A45D 29/00 132/73 |
| 5,876,663 | A * | 3/1999 | Laroussi | A61L 2/14 210/764 |
| 6,150,755 | A * | 11/2000 | Druz | H01J 27/16 313/359.1 |
| 7,192,553 | B2 * | 3/2007 | Crowe | A61L 9/22 422/23 |
| 7,368,542 | B2 * | 5/2008 | McIntyre | G01N 33/5375 530/427 |
| 7,812,307 | B2 * | 10/2010 | Dutton | H01J 37/32366 250/288 |
| 9,067,273 | B1 * | 6/2015 | Kim | H05H 1/2406 |
| 9,169,317 | B2 * | 10/2015 | McIntyre | G01N 33/564 |
| 9,255,330 | B2 * | 2/2016 | Vangeneugden | H01J 37/32091 |
| 9,288,886 | B2 * | 3/2016 | Koo | H01J 37/32348 |
| 9,351,792 | B2 * | 5/2016 | Manstein | A61B 18/203 |
| 9,363,880 | B2 * | 6/2016 | Keener | A23L 3/263 |
| 9,750,951 | B2 * | 9/2017 | Kim | A61K 33/00 |
| 9,757,196 | B2 * | 9/2017 | Moss | A61B 18/1477 |
| 9,861,829 | B2 * | 1/2018 | Jacofsky | A61B 17/3421 |
| 10,039,927 | B2 * | 8/2018 | Watson | H05H 1/2406 |
| 10,493,263 | B2 * | 12/2019 | Roe | A61K 45/06 |
| 10,517,674 | B2 * | 12/2019 | Varghese | A61B 18/203 |
| 10,524,848 | B2 * | 1/2020 | Sartor | A61B 17/00234 |
| 10,624,696 | B2 * | 4/2020 | Deem | A61B 18/18 |
| 10,736,780 | B2 * | 8/2020 | Schuele | A61B 3/1025 |
| 11,102,877 | B2 * | 8/2021 | Eckert | H05H 1/2406 |
| 11,167,146 | B2 * | 11/2021 | Canady | A61K 33/00 |
| 2002/0187066 | A1 * | 12/2002 | Yu | A61L 2/0011 422/23 |
| 2005/0101016 | A1 * | 5/2005 | McIntyre | A61P 7/04 530/383 |
| 2006/0278254 | A1 * | 12/2006 | Jackson | H01J 37/3244 257/E21.228 |
| 2013/0109838 | A1 * | 5/2013 | McIntyre | A61P 25/10 530/387.1 |
| 2014/0171854 | A1 | 6/2014 | Jacofsky et al. | |
| 2015/0352516 | A1 * | 12/2015 | Imada | B01J 19/088 422/186.04 |
| 2015/0366042 | A1 * | 12/2015 | Zaidi | H05H 1/2406 315/111.21 |
| 2016/0296763 | A1 * | 10/2016 | Kim | H05H 1/24 |
| 2017/0189349 | A1 * | 7/2017 | Roe | A61K 31/025 |
| 2017/0354616 | A1 * | 12/2017 | Roe | A61K 33/00 |
| 2017/0354815 | A1 * | 12/2017 | Roe | A61K 33/00 |
| 2018/0177550 | A1 * | 6/2018 | Anderson | A61B 18/203 |
| 2020/0113986 | A1 * | 4/2020 | Ye | A61K 35/12 |
| 2020/0179709 | A1 * | 6/2020 | Kim | A61N 1/44 |

FOREIGN PATENT DOCUMENTS

| | | | |
|---|---|---|---|
| KR | 101248668 | 3/2013 | |
| KR | 20130099522 | 9/2013 | |
| KR | 20150065147 | 6/2015 | |
| KR | 20150084146 | 7/2015 | |
| KR | 101577207 | 12/2015 | |
| KR | 101657063 | 9/2016 | |
| WO | WO-2005125286 A2 * | 12/2005 | ........... H05H 1/2406 |
| WO | 2016096751 | 6/2016 | |

OTHER PUBLICATIONS

International Search Report—PCT/KR2017/010235 dated Feb. 19, 2018.

* cited by examiner

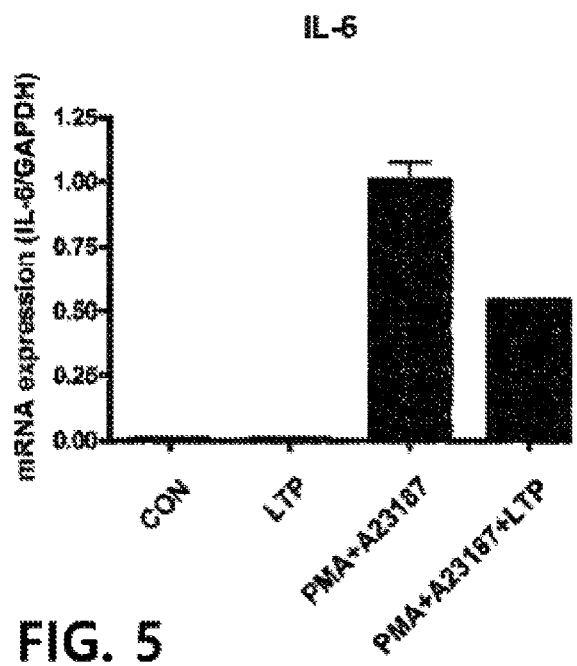
FIG. 5
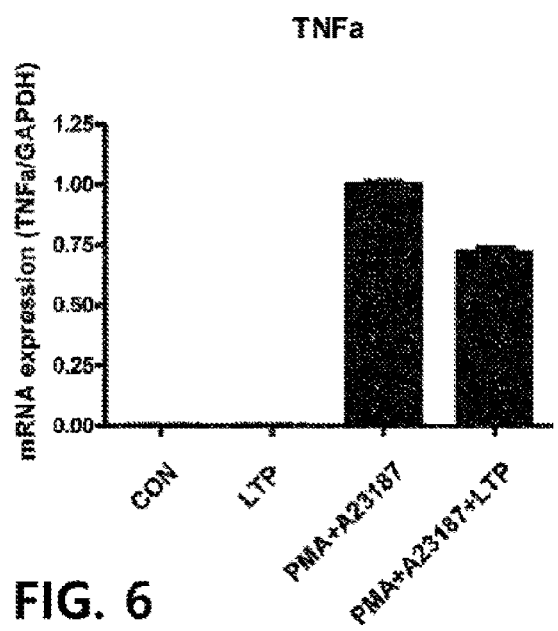
FIG. 6
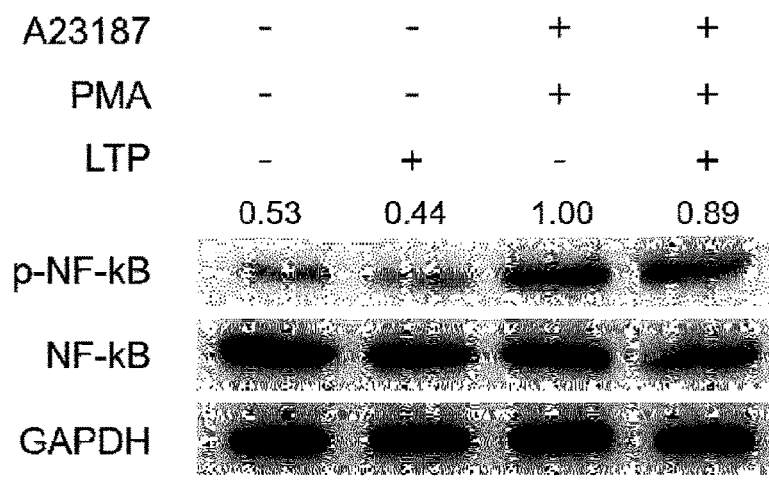
FIG. 7
FIG. 8
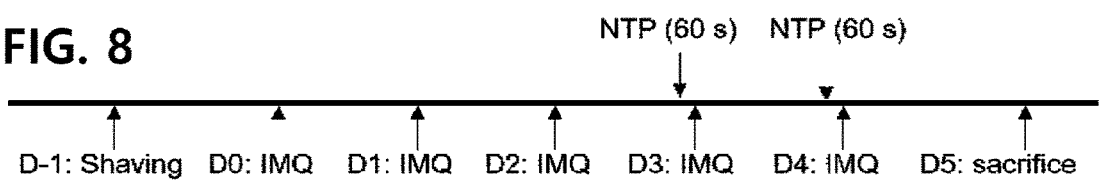

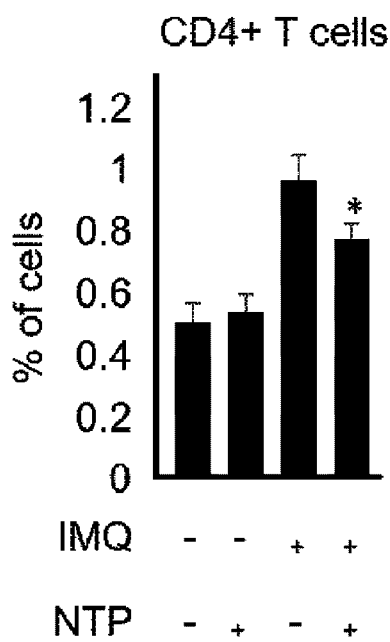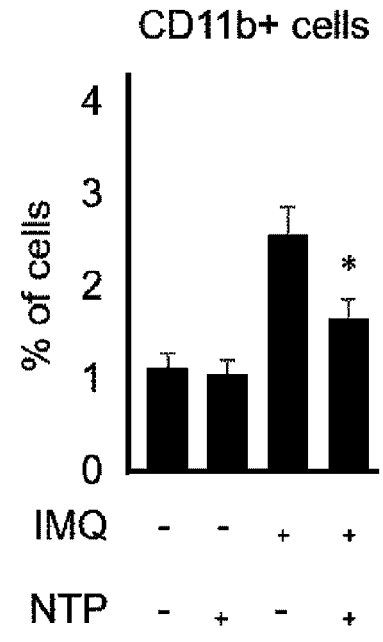
FIG. 12A   FIG. 12B
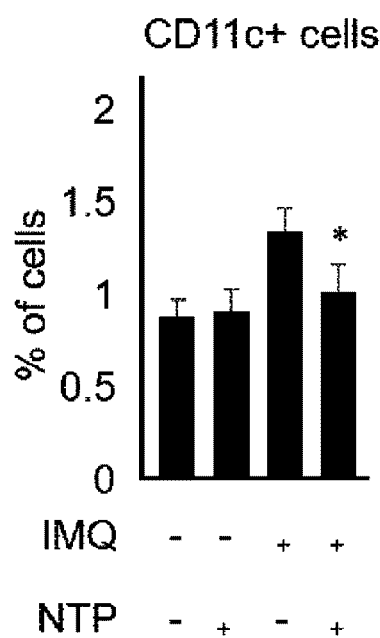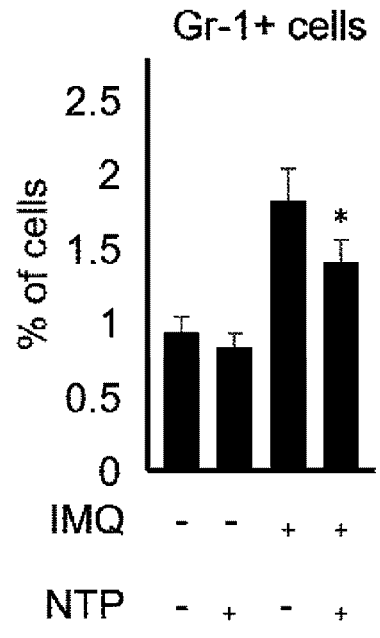
FIG. 12C   FIG. 12D

NTP

LTP

```
                      SEQUENCE LISTING

<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: hIL-1beta forward primer

<400> SEQUENCE: 1
acagatgaag tgctccttcc a                                            21

<210> SEQ ID NO 2
<211> LENGTH: 21
<212> TYPE: DNA
<213> ORGANISM: Artificial
<220> FEATURE:
<223> OTHER INFORMATION: hIL-1beta reverse primer

<400> SEQUENCE: 2
gtcggagatt cgtagctgga t                                            21

<210> SEQ ID NO 3
<211> LENGTH: 24
<212> TYPE: DNA
<213> ORGANISM: Artificial
<220> FEATURE:
<223> OTHER INFORMATION: hIL-8 forward primer

<400> SEQUENCE: 3
```

```
atgacttcca agctggccgt ggct                                          24
```

<210> SEQ ID NO 4
<211> LENGTH: 24
<212> TYPE: DNA
<213> ORGANISM: Artificial
<220> FEATURE:
<223> OTHER INFORMATION: hIL-8 reverse primer

<400> SEQUENCE: 4

```
tctcagccct cttcaaaaac ttct                                          24
```

<210> SEQ ID NO 5
<211> LENGTH: 21
<212> TYPE: DNA
<213> ORGANISM: Artificial
<220> FEATURE:
<223> OTHER INFORMATION: hIL-10 forward primer

<400> SEQUENCE: 5

```
catcgatttc ttccctgtga a                                             21
```

<210> SEQ ID NO 6
<211> LENGTH: 24
<212> TYPE: DNA
<213> ORGANISM: Artificial
<220> FEATURE:
<223> OTHER INFORMATION: hIL-10 reverse primer

<400> SEQUENCE: 6

```
tcttggagct tattaaggc attc                                           24
```

<210> SEQ ID NO 7
<211> LENGTH: 24
<212> TYPE: DNA
<213> ORGANISM: Artificial
<220> FEATURE:
<223> OTHER INFORMATION: hIFN-gamma forward primer

<400> SEQUENCE: 7

```
ctaattattc ggtaactgac ttga                                          24
```

<210> SEQ ID NO 8
<211> LENGTH: 21
<212> TYPE: DNA
<213> ORGANISM: Artificial
<220> FEATURE:
<223> OTHER INFORMATION: hIFN-gamma reverse primer

<400> SEQUENCE: 8

```
acagttcagc catcacttgg a                                             21
```

<210> SEQ ID NO 9
<211> LENGTH: 19
<212> TYPE: DNA
<213> ORGANISM: Artificial
<220> FEATURE:
<223> OTHER INFORMATION: hTGF-beta1 forward primer

<400> SEQUENCE: 9

```
cccagcatct gcaaagctc                                                19
```

<210> SEQ ID NO 10
<211> LENGTH: 20
<212> TYPE: DNA
<213> ORGANISM: Artificial

```
<220> FEATURE:
<223> OTHER INFORMATION: hTGF-beta1 reverse primer

<400> SEQUENCE: 10
gtcaatgtac agctgccgca                                              20
```

COMPOSITION FOR ATOPY OR PSORIASIS TREATMENT COMPRISING LIQUID TYPE PLASMA

The invention was made with government support under Serial No. 2017M3A9F7079339 awarded by Ministry of Science and ICT (Republic of Korea).

TECHNICAL FIELD

The present invention relates to a composition for treating atopyor psoriasis, which includes plasma-treated liquid material. More particularly, the present invention relates to a method of producing plasma-treated liquid material for preventing or treating atopic dermatitis, a pharmaceutical composition for preventing or treating atopic dermatitis using plasma-treated liquid material produced using the method, and a method of preventing or treating atopic dermatitis using the plasma-treated liquid material. In addition, the present invention relates to a method of producing plasma-treated liquid material for preventing or treating psoriasis, a pharmaceutical composition for preventing or treating psoriasis using plasma-treated liquid material produced using the method, and a method of preventing or treating psoriasis using the plasma-treated liquid material.

BACKGROUND ART

Atopic dermatitis, which is a typical atopic skin disease, is chronic and persistent skin inflammation accompanied by severe itching and consequent secondary infections. Many western people have this disease, about 10% of children are suffering from this disease, and an increase in atopic dermatitis has continued in recent years. Atopic dermatitis is also rapidly increasing in Korea, but treatment for this is not easy and the cause of this disease is not identified. Thus, most cases are dependent on symptomatic treatment. Recently, as it has been found that atopic dermatitis is caused by immunological abnormalities, new therapies for this have been attempted.

Inadequate or sensitive immune responses are referred to as hypersensitivity. Type 1 hypersensitivity allergic diseases are induced by antigen-specific IgE antibodies, and since these responses may not occur or may occur easily even when exposed to the same antigen, depending on individuals. These responses are also referred to as atopy which means idiosyncratic reactions. Examples of atopy include allergic rhinitis, asthma, a food allergy, atopic dermatitis, and the like.

T-helper (Th) cells, which are responsible for the immune function in humans, differentiate into subtypes Th1 and Th2, which secrete cytokines that are in balance with each other and inhibit each other's function. However, in patients with atopic dermatitis, Th2 cells are more abundant than Th1 cells, resulting in an imbalance between them. That is, the secretion of eosinophils involved in allergies and interleukin (IL)-4, IL-5, IL-10, and the like that increase IgE antibodies increases in Th2 cells, whereas the secretion of substances that inhibit the production of IgE decreases in Th1 cells. Eosinophils and mast cells are activated by the increased IgE. When an IgE antibody binds to an IgE receptor (FcεRI) and an allergen cross-links two FcεRI/IgE conjugates to activate cells, the degranulation of intracellular granules occurs. At this time, physiologically active substances such as histamine, leukotrienes, and the like are extracellularly secreted, thereby inducing atopic dermatitis symptoms such as strong itching, erythema, edema, inflammation, and the like (Cellular and Molecular Immunology, Abbas et al., 2nd Edition, Saunders, Philadelphia, Journal of Dermatological Science, 36, 1-9, 2004).

Currently, medicines such as steroids, antihistamines, and the like are widely used in treating atopic dermatitis, and immunosuppressants are used for severe cases. However, most of these drugs have temporary efficacy and have many serious side effects, such as osteoporosis, avascular necrosis, arteriosclerosis, glaucoma, carcinogenicity, and the like. Therefore, to alleviate and treat atopic dermatitis, there is an urgent need to develop a new therapeutic agent that has a good treatment effect, has fewer side effects, and exhibits a sustained therapeutic effect.

Meanwhile, NF-kB is known as a transcription factor that increases the expression of substances involved in immune responses or inflammatory responses by operating a gene expression mechanism that causes inflammation, such as tumor necrosis factor-α (TNF-α), interleukin-1 (IL-1), IL-6, IL-8, GM-CSF, inducible nitric oxide synthase (iNOS), intercellular adhesion molecule 1 (ICAM-1), E-selectin, MHC class I and II molecules, and the like. Thus, the regulation of NF-kB activity may be effectively used in treating chronic and acute inflammatory diseases, and NF-kB inhibitors are expected to exhibit an atopic dermatitis therapeutic effect.

Psoriasis is an immune-mediated autoimmune skin disease induced by chronic activation of inflammatory cell infiltration in the skin and dysregulation of epidermal keratinocytes. Histologically, psoriasis is considered to be thickening and scaling of the epidermis and hyperproliferative parakeratosis in a skin biopsy. The pathogenic mechanism of psoriasis has not yet been completely identified and has been reported to be related to complex mechanisms including interactions between inflammatory cytokines and infiltration of immune cells, such as T cells, and recent studies have reported that T helper 17 (Th17) cells and Th17-mediated cytokines such as IL-17A, IL-22, and IL-23 induce psoriasis triggering.

Examples of the general treatment of psoriasis include topical administration, phototherapy, and internal administration. The topical administration is a treatment method including steroids, coal tar, anthralin, vitamin D3 and analogs thereof, retinoids, sunlight, and the like, and such topical treatment has side effects such as skin thinning, stretch marks, burns, irritation, and photosensitivity. In addition, steroids can induce resistance, thus affecting subsequent steroid treatments. The phototherapy includes the administration of psoralen together with ultraviolet B or ultraviolet A, and is disadvantageous in that skin aging rapidly occurs and the incidence rate of skin cancer increases. The internal administration is currently the most widely used method in which an immunomodulator, such as a cyclosporine, is administered. However, this method causes nephrotoxicity or hypertension due to prolonged use. Therefore, the development of a therapeutic method that addresses the current problems of psoriasis treatment and is capable of effectively treating psoriasis is a major research subject, and research thereon has been conducted, but effective treatment for psoriasis has not yet been reported.

Meanwhile, low-temperature atmospheric-pressure plasma refers to plasma in which, among ions and electrons constituting plasma, the energy of the electrons is greater than the energy of the ions, and is also referred to as low-temperature normal-pressure plasma. That is, low-temperature plasma is produced in a such a way that, when high-pressure electric discharge is performed on a discharge gas, electrons generated by discharge collide with molecules of the discharge gas and, as a result, an outer electron state of gas molecules is changed, and refers to a gas in an electrically neutral state formed as a result of a radical, which is a chemically active species with high reactivity (e.g., OH, COOH, CHO, or the like), excited molecules, and ions being positively or negatively charged. Plasma is divided into high-temperature thermal plasma in which temperatures of electrons, ions, and molecules are all high, and low-temperature plasma in which only the temperature of electrons is high. High-temperature thermal plasma is utilized in melting a material due to a high-temperature characteristic thereof, and low-temperature plasma may be applied to materials or conditions to which high temperatures cannot be applied since only the temperature of electrons is high and an apparatus thereof is simple. Such plasma induces various chemical reactions, and thus many studies on utilizing the plasma and applying it to various fields have been conducted. However, there is still no report of a method of treating psoriasis using this.

Therefore, the applicants of the present invention completed the present invention. The present invention relates to a composition for treating atopy or psoriasis, which includes plasma-treated liquid material, and the plasma-treated liquid material of the present invention has a significant effect of inhibiting immune hypersensitivity reactions and has an effect of inhibiting the generation and proliferation of psoriasis, and thus is expected to be greatly utilized in preventing and treating immune hypersensitivity reactions including atopic dermatitis and psoriasis.

DISCLOSURE

Technical Problem

The present invention has been made to address the above-described problems of the related art, and relates to a composition for treating atopy or psoriasis, which includes plasma-treated liquid material.

As a result of having made intensive efforts to develop a method capable of addressing the problems of existing atopic dermatitis therapeutic agents and for the fundamental treatment of atopic dermatitis, the inventors of the present invention discovered plasma-treated liquid material capable of preventing or treating atopic dermatitis by inhibiting the activity of mast cells, and thus completed the present invention. An object of the present invention is to provide a method of producing plasma-treated liquid material for preventing or treating atopic dermatitis, a pharmaceutical composition for preventing or treating atopic dermatitis using plasma-treated liquid material produced using the method, and a method of preventing or treating atopic dermatitis using the plasma-treated liquid material. The plasma-treated liquid material according to the present invention may inhibit the activity of various factors related to immune hypersensitivity reactions, such as STAT6, NF-kB, and the like, and mast cells important for allergic responses. Thus, it is anticipated that the plasma-treated liquid material according to the present invention may be effectively used in preventing or treating atopic dermatitis.

In addition, the plasma-treated liquid material of the present invention has a significant effect on inhibiting the induction and progress of psoriasis.

Therefore, an object of the present invention is to provide a method of producing plasma-treated liquid material for preventing or treating atopic dermatitis or psoriasis, a pharmaceutical composition for preventing or treating atopic dermatitis or psoriasis using plasma-treated liquid material produced by the method, and a method of preventing or treating atopic dermatitis or psoriasis using plasma-treated liquid material produced by the method.

However, technical problems to be solved by the present invention are not limited to the above-described technical problems, and other unmentioned technical problems will become apparent from the following description to those of ordinary skill in the art.

Technical Solution

Hereinafter, various embodiments of the present invention will be described with reference to the accompanying drawings. In the following description, for the purposes of complete understanding of the present invention, various specific details, such as specific forms, compositions, and processes, and the like, will be provided. However, specific embodiments may be practiced without one or more of these specific details, or with other known methods and forms. In other examples, known processes and manufacturing techniques will not be described in detail in order to not unnecessarily obscure the present invention. Reference throughout the present specification to "one embodiment" or "embodiments" indicates that particular features, forms, compositions, or characteristics described in connection with embodiments are included in one or more embodiments of the present invention. Accordingly, conditions of "one embodiment" or "embodiments" described in various locations throughout the present specification do not indicate the same embodiment of the present invention. In addition, particular features, forms, compositions, or characteristics may be combined in any suitable manner in one or more embodiments.

In one embodiment of the present invention, the term "psoriasis" refers to an erythermatous skin lesion covered with silvery white scales that have a definite boundary (a light gray substance that occurs when the skin exfoliates), and psoriasis mainly occurs in greatly irritated areas, such as the elbows, knees, buttocks, scalp, and the like. Psoriasis appears as various clinical symptoms including papules (rashes occurring on the skin surface, among the symptoms of skin diseases), plaque, pustular or exfoliative psoriasis, psoriatic arthritis, and the like, and is a chronic inflammatory skin disease in which aggravation and improvement are repeated in some cases. Psoriasis may be further classified into plaque psoriasis, intertriginous psoriasis, guttate psoriasis, pustular psoriasis, erythrodermic psoriasis, and the like. Specifically, plaque psoriasis is most commonly observed as a typical clinical form of psoriasis. Individual lesions are in the form of plaques having a clear boundary with the surroundings, reddish, and covered with silvery white scales, and the lesions commonly occur at sites such as the elbows, knees, buttocks, scalp, and the like, and symmetrically occur. A chronic plaque form is referred to as psoriasis vulgaris. Intertriginous psoriasis refers to a rare case in which psoriasis occurs at a site where the skin folds such as the armpit and groin, and is also referred to as flexural psoriasis or inverse psoriasis. In the case of guttate psoriasis, drop-shaped papules having a size of 0.5 cm to 1.5 cm are systemically distributed and rapidly occur after tonsillitis caused by streptococci. In a patient's blood test, an anti-streptolysin O (ASO) level may increase. Pustular psoriasis is an acute form of psoriasis that is rarely seen, and there are local pustular psoriasis in which pustules appear on the palms and soles, and systemic pustular psoriasis in which pustules appear on the whole body. Acute systemic forms include systemic symptoms such as chills, high fever, malaise, arthralgia, and the like, and may be accompanied by leukocytosis. Lastly, erythrodermic psoriasis is an acute form of psoriasis that is accompanied by erythema and scaling throughout the skin. A severe scaling case is also referred to as exfoliative psoriasis. In severe cases, severe itching occurs and the symptom invades the face. Psoriatic arthritis is seen in about 5% to about 10% of patients with psoriasis. There are various clinical forms of psoriatic arthritis, such as asymmetric involvement of one or a few joints, involvement of distal interphalangeal joints, a form that symmetrically causes polyarthritis, an arthritis mutilans type that causes severe deformation of joints, a spondylitis type, and the like. In addition, in many cases, most patients with psoriasis have lesions under fingernails and toenails.

According to research results accumulated so far, it is understood that psoriasis is generated in such a way that, in people having genetic etiologic factors for psoriasis, psoriasis-related T lymphocytes are activated by stimulation of a psoriasis antigen, consequently generated cytokines induce hyperproliferation of keratinocytes, and skin-specific CLA+T lymphocytes are continuously introduced into skin lesions. Thus, psoriasis lesions are classified as a chronic T lymphocyte-mediated autoimmune disease. As a skin region of the T lymphocyte-mediated autoimmune disease, a T lymphocyte-mediated skin disease may be used in the same sense, and the T lymphocyte-mediated skin disease may be any one or more selected from the group consisting of systemic lupus erythematosus, cutaneous lupus erythematosus, scleroderma, psoriasis, dermatomyositis, and chronic dermatitis, but the present invention is not limited thereto.

In one embodiment of the present invention, the term "non-thermal atmospheric pressure plasma" refers to an ionized gas that satisfies Debye shielding. This is considered to be another state of matter, which represents a fourth state, other than the three states of matter: gas, liquid, and solid. In the plasma according to the present invention, electrons and cations may be generated by excitation and ionization of a neutral gas through phase transition of the neutral gas into plasma by an external voltage, and a radical generated by excitation of a molecular gas may be present. A plasma generator may be any known plasma generator without limitation as long as it is capable of producing low-temperature atmospheric-pressure plasma in accordance with the purposes of the present invention, and nitrogen gas is preferably used, but the present invention is not limited thereto.

In one embodiment of the present invention, the term "plasma-conditioned liquid" or "plasma-treated liquid material" may be produced by treatment of liquid with non-thermal atmospheric pressure plasma (NTP). The terms "plasma-conditioned liquid" and "plasma-treated liquid material" may be used interchangeably with the term "liquid type plasma (LTP)," and the term "liquid material" refers to any material in a liquid state without limitation, but the liquid material is preferably water, saline, buffer, or culture media, and culture media is most preferably used.

The plasma-treated liquid material of the present invention may be supplied in the form of a liquid composition, and thus is easily distributed and highly portable, and may provide both moisturizing and treatment for atopy and psoriasis in which moisturizing is important. In addition, the plasma-treated liquid material of the present invention has less damage to cells as compared to a case in which skin with atopy or psoriasis is directly treated with plasma, has no risk of skin damage, such as burns or the like due to a user's erroneous operation of a device, and has uniform applicability even over a wide and curved area.

In one embodiment of the present invention, the term "culture media" refers to culture media capable of supporting the growth and survival of cells in vitro, and includes all media generally used in the art, which are suitable for use in culturing cells. Media and culture conditions may be selected depending on the type of cells. A basic medium used in culturing cells is preferably a cell culture minimum medium (CCMM), and generally includes a carbon source, a nitrogen source, and a trace element component. Examples of the basic medium for culturing cells include, but are not limited to, Dulbeco's Modified Eagle's Medium (DMEM), Minimal Essential Medium (MEM), Basal Medium Eagle (BME), RPMI1640, F-10, F-12 (Minimal Essential Medium), Glasgow's Minimal Essential Medium (GMEM), and Iscove's Modified Dulbecco's Medium.

In one embodiment of the present invention, the term "treatment" means all actions that improve or beneficially change the symptoms of atopic dermatitis or psoriasis and diseases due to this by using the plasma-treated liquid material according to the present invention. Those of ordinary skill in the art to which the present invention pertains will be able to understand the accurate criteria of atopic dermatitis or psoriasis with reference to data provided by the Korean Medical Association, and the like and determine the degrees of alleviation, improvement, and treatment.

In one embodiment of the present invention, the term "prevention" means all actions that inhibit or delay the onset of atopic dermatitis or psoriasis and other diseases due to this by using the plasma-treated liquid material according to the present invention. It will be obvious to those of ordinary skill in the art that the composition of the present invention having an effect of treating atopic dermatitis or psoriasis is able to prevent these diseases by using the plasma-treated liquid material of the present invention before initial symptoms or symptoms of atopic dermatitis or psoriasis occur.

As used herein, the term "pharmaceutical composition" refers to a composition to be administered for a specific purpose. For the purpose of the present invention, the pharmaceutical composition of the present invention includes, as an active ingredient, plasma-treated liquid material produced by irradiating a liquid material with plasma, and may include a protein involved therein and a pharmaceutically acceptable carrier, an excipient or a diluent. The term "pharmaceutically acceptable" carrier or excipient means a carrier or excipient approved by the government regulatory department, or listed in the pharmacopoeia approved by the government or other generally approved pharmacopoeia, for use in vertebrates, more particularly, humans.

For parenteral administration, the pharmaceutical compositions of the present invention may be in the form of a suspension, solution or emulsion in an oily or aqueous carrier and may be produced in the form of a solid or semi-solid. In addition, the pharmaceutical composition of the present invention may include a formulating agent such as a suspending agent, a stabilizing agent, a solubilizing agent, and/or a dispersing agent, and may be sterilized. The pharmaceutical composition may be stable under preparation and storage conditions and may be preserved against the contaminating action of microorganisms such as bacteria or fungi. Alternatively, the pharmaceutical composition of the invention may be in a sterile powder form for reconstitution with a suitable carrier before use. The pharmaceutical composition may be present, as a unit-dose form, in micro needle patches or ampoules, in other unit-dose containers, or in multi-dose containers. Alternatively, the pharmaceutical composition may be stored under a freeze-dried (lyophilized) condition requiring only the addition of a sterile liquid carrier, e.g., water for injection immediately before use. Immediately, an injection solution and a suspension may be produced into the form of sterile powder, granules, or tablets.

In some non-limiting embodiments, the pharmaceutical composition of the present invention may be formulated, or may be included in the form of microspheres in a liquid. In certain non-limiting embodiments, the pharmaceutical composition of the present invention may include a pharmaceutically acceptable compound and/or a mixture thereof at a concentration between 0.001 U/kg and 100,000 U/kg. In addition, in certain non-limiting embodiments, the pharmaceutical composition of the present invention may include suitable excipients such as a preservative, a suspending agent, an additional stabilizing agent, a dye, a buffer, an antimicrobial agent, an antifungal agent, and an isotonic agent, e.g., sugar or sodium chloride. As used herein, the term "stabilizing agent" refers to a compound that is optionally used in the pharmaceutical composition of the present invention to increase shelf life. In non-limiting embodiments, the stabilizing agent may be a sugar, an amino acid, or a polymer. In addition, the pharmaceutical composition of the present invention may include one or more pharmaceutically acceptable carriers, and the carriers may be solvents or dispersion media. Non-limiting examples of pharmaceutically acceptable carriers include water, saline, ethanol, polyols (e.g., glycerol, propylene glycol and liquid polyethylene glycol), oils, and suitable mixtures thereof. Non-limiting examples of sterilization techniques applied to the pharmaceutical composition of the present invention include filtration through a bacteria-inhibiting filter, terminal sterilization, incorporation of sterile preparations, irradiation, gas irradiation, sterilization, heating, vacuum drying, and lyophilization.

As used herein, the term "administration" means introduction of the composition of the present invention to a patient in any suitable manner, and the composition of the present invention may be administered through any general route as long as it enables the composition to reach target tissue therethrough. The composition of the present invention may be administered via routes such as oral administration, intraperitoneal administration, intravenous administration, intramuscular administration, subcutaneous administration, intradermal administration, intranasal administration, intrapulmonary administration, intrarectal administration, intraperitoneal administration and intrathecal administration, but it is not preferable that the pharmaceutical composition of the present invention is applied on the skin or injected subcutaneously or intradermally, but the present invention is not limited thereto.

The treatment method of the present invention may include administering the pharmaceutical composition in a pharmaceutically effective amount. In the present invention, the effective amount may be adjusted depending on various factors including the type of disease, the severity of disease, the types and amounts of the active ingredient included in the composition and other ingredients, the type of formulation, the age and body weight of a patient, general health conditions, gender and diet, administration time, administration routes, an excretion rate of the composition, treatment periods, and simultaneously used drugs.

According to one embodiment of the present invention, there is provided a method of producing plasma-treated liquid material for the prevention or treatment of an allergic disease, including: (a) filling a plasma generator with a carrier gas; (b) supplying a voltage of 1 kV to 13 kV and a frequency of 15 kHz to 30 kHz to the plasma generator to generate plasma; and (c) irradiating a liquid material with the generated plasma, wherein, in process (a), the carrier gas includes any one or more selected from the group consisting of nitrogen, helium, argon, and oxygen, the irradiation of process (c) is performed at a distance of 0.1 cm to 15 cm from a surface of the liquid material for 5 minutes to 30 minutes, the liquid material of process (c) is water, saline, a buffer, or a medium, and the allergic disease is allergic rhinitis, asthma, a food allergy, or atopic dermatitis.

According to anther embodiment of the present invention, there is provided a pharmaceutical composition for the prevention or treatment of an allergic disease, which includes, as an active ingredient, plasma-treated liquid material produced using any one or more of the above-described methods, wherein the pharmaceutical composition is formulated into an oral preparation, a parenteral preparation, or a topical preparation, the pharmaceutical composition is used alone or in combination with surgery, radiotherapy, hormone treatment, chemotherapy, and methods using a biological response modifier, and the allergic disease is allergic rhinitis, asthma, a food allergy, or atopic dermatitis.

According to another embodiment of the present invention, there is provided a method of preventing or treating an allergic disease, which includes administering any one or more of the above-described pharmaceutical compositions to an individual, wherein the allergic disease is allergic rhinitis, asthma, a food allergy, or atopic dermatitis.

According to another embodiment of the present invention, there is provided a use of any one or more of the pharmaceutical compositions for preventing or treating an allergic disease, wherein the allergic disease is allergic rhinitis, asthma, a food allergy, or atopic dermatitis.

According to another embodiment of the present invention, there is provided a method of producing plasma-treated liquid material for the prevention or treatment of a T lymphocyte-mediated skin disease, including: (a) filling a plasma generator with a carrier gas; (b) supplying a voltage of 5 kV to 20 kV and a frequency of 10 kHz to 30 kHz to the plasma generator to generate plasma; and (c) treating a liquid material with the generated plasma, wherein, in process (a), the carrier gas includes any one or more selected from the group consisting of nitrogen, helium, argon, and oxygen, the treatment of process (c) is performed at a distance of 0.1 cm to 15 cm from a surface of the liquid material for 5 minutes to 120 minutes, the liquid material of process (c) is water, saline, a buffer, or a medium, and the T lymphocyte-mediated skin disease includes any one or more selected from the group consisting of systemic lupus erythematosus, cutaneous lupus erythematosus, scleroderma, psoriasis, dermatomyositis, and chronic dermatitis.

According to another embodiment of the present invention, there is provided a pharmaceutical composition for the prevention or treatment of a T lymphocyte-mediated skin disease, which includes, as an active ingredient, plasma-treated liquid material produced using any one or more of the above-described methods, wherein the pharmaceutical composition is formulated into an oral preparation, a parenteral preparation, or a topical preparation, the pharmaceutical composition is used alone or in combination with surgery, radiotherapy, hormone treatment, chemotherapy, and methods using a biological response modifier, and the T lymphocyte-mediated skin disease includes any one or more selected from the group consisting of systemic lupus erythematosus, cutaneous lupus erythematosus, scleroderma, psoriasis, dermatomyositis, and chronic dermatitis.

According to another embodiment of the present invention, there is provided a method of preventing or treating a T lymphocyte-mediated skin disease, which includes administering any one or more of the pharmaceutical compositions to an individual, wherein the T lymphocyte-mediated skin disease includes any one or more selected from the group consisting of systemic lupus erythematosus, cutaneous lupus erythematosus, scleroderma, psoriasis, dermatomyositis, and chronic dermatitis.

According to another embodiment of the present invention, there is provided a use of any one or more of the pharmaceutical compositions for the prevention or treatment of a T lymphocyte-mediated skin disease, wherein the T lymphocyte-mediated skin disease includes any one or more selected from the group consisting of systemic lupus erythematosus, cutaneous lupus erythematosus, scleroderma, psoriasis, dermatomyositis, and chronic dermatitis.

Hereinafter, the present invention will be described in detail step by step.

Advantageous Effects

The present invention relates to a composition for treating atopy or psoriasis, which includes plasma-treated liquid material, and the plasma-treated liquid material of the present invention has a significant effect of inhibiting immune hypersensitivity reactions and has an effect of inhibiting the generation and proliferation of psoriasis, and thus is expected to be greatly utilized in preventing and treating immune hypersensitivity reactions including atopic dermatitis or psoriasis.

DESCRIPTION OF DRAWINGS

FIG. 5 is a graph showing the results of confirming an expression level of IL-6 in mast cells stimulated with PMA and A23187 and treated with plasma-treated liquid material, according to an embodiment of the present invention.

FIG. 6 is a graph showing the results of confirming an expression level of TNF-α in mast cells stimulated with PMA and A23187 and treated with plasma-treated liquid material, according to an embodiment of the present invention.

FIG. 7 is a graph showing the results of confirming the inhibition of NF-kB activity in mast cells stimulated with PMA and A23187 and treated with plasma-treated liquid material, according to an embodiment of the present invention.

FIG. 8 illustrates a time frame for IMQ and/or NTP treatment to verify an effect of plasma on treating psoriasis, according to an embodiment of the present invention.

FIGS. 12A to 12D are graphs showing changes in infiltration amounts of CD4+ T cells, CD11c+ cells, CD11b+ cells, and Gr-1+ cells by IMQ stimulation and NTP treatment, according to one embodiment of the present invention.

BEST MODE

To confirm the effect of plasma-treated liquid material treatment on atopic dermatitis, western blotting was carried out using a human keratinocyte cell line (HaCaT) and mast cells to confirm protein expression amounts of p-STAT6 (Abcam) and STAT6 (Cell Signaling Technology). IL-4 is a hypersensitive activity factor and is known to promote allergic responses. As an experimental result, phosphorylation of a transcriptional activator (p-STAT6) was significantly reduced in the group treated with IL-4 and plasma-treated liquid material (LTP) as compared with the group treated with IL-4 alone. This means that the plasma-treated liquid material treatment can remarkably alleviate immune hypersensitivity reactions.

In addition, to confirm an inflammatory inhibitory effect of plasma-treated liquid material on psoriasis-like skin, it was examined whether plasma-treated liquid material affected STAT3 activation in HaCaT cells. STAT3 activation is known to play an important role in Th17 cell differentiation and the onset of psoriasis. As an experimental result, it was confirmed that plasma-treated liquid material treatment inhibited STAT3 activation (pSTAT3) in IL-6-stimulated HaCaT cells. These results suggest that plasma-treated liquid material may inhibit the STATS signaling pathway and result in suppression of psoriasis in mice.

Mode of the Invention

Hereinafter, the present invention will be described in further detail with reference to the following examples. It will be obvious to those of ordinary skill in the art that these examples are provided only to more particularly describe the present invention and are not intended to limit the scope of the present invention in accordance with the essence of the present invention.

Example 1. Confirmation of Treatment Effect of Plasma-Treated Liquid Material on Atopic Dermatitis Example 1-1. Confirmation of Plasma Treatment Effect on Atopic Dermatitis To confirm the effect of plasma treatment on atopic dermatitis, NC/Nga mice (6 weeks old, male, Orient Bio, Korea) were randomly selected and treated as shown in Table 1.

TABLE 1

| Group | Remarks |
| --- | --- |
| Negative control | Non-treatment |
| Positive control | Treatment with biostir (Biostir only) |
| Plasma control | Treatment with plasma (NTP) (NTP only) |
| Plasma experimental group | After treatment with Biostir, plasma (NTP) is treated (Biostir + NTP) |

Specifically, the dorsal hairs of the mice were completely removed, 200 μl of 4% SDS solution was applied to destroy the skin barrier, and biostir (house dust mite), which is an atopic dermatitis inducer, was treated every 4 days for a total of 3 weeks. For the plasma treatment group, plasma generated by maintaining a gas flow rate of 10 L/min, a voltage of 15 kVp-p, and a frequency of 15 kHz was irradiated using a plasma generator using nitrogen ($N_2$) gas as a source of a non-thermal atmospheric pressure plasma.

Figure 1:
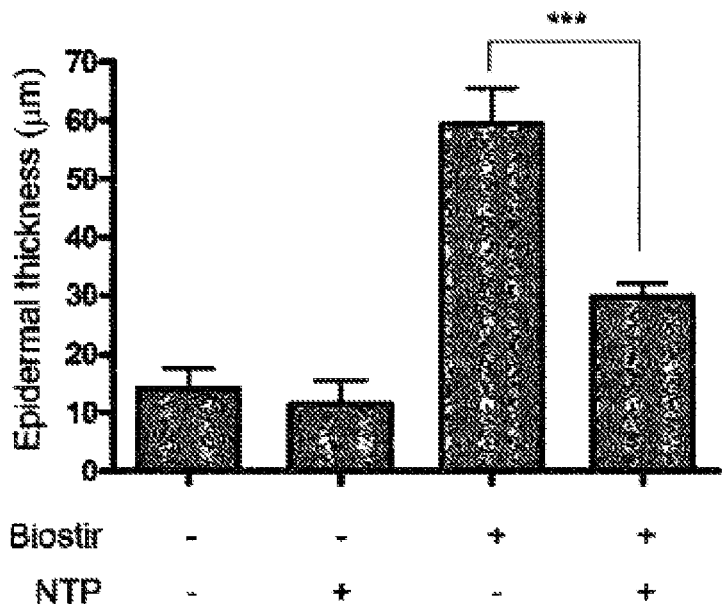
FIG. 1 is a graph showing H & E staining results of skin tissues of NC/Nga mice treated with an atopic dermatitis-inducing factor and/or plasma, according to an embodiment of the present invention.
Figure 2:
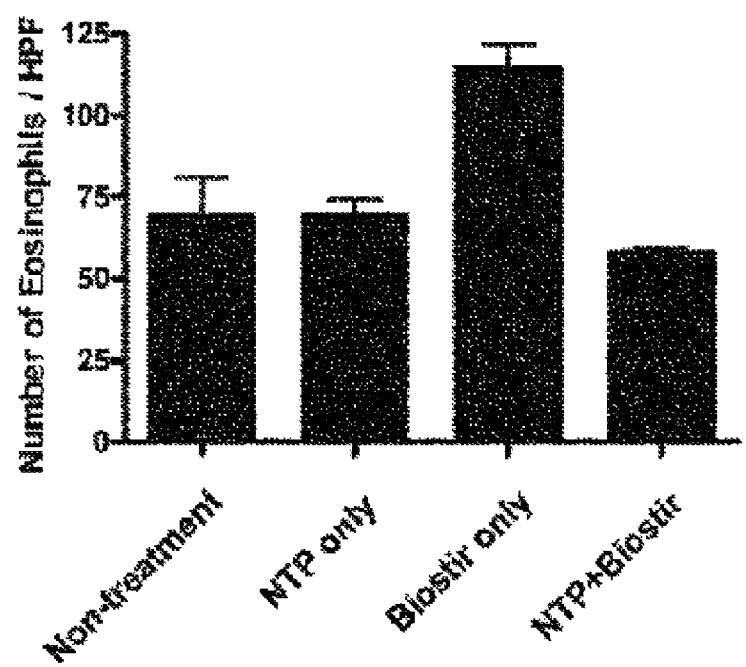
FIG. 2 is a graph showing toluidine blue staining results of skin tissues of NC/Nga mice treated with an atopic dermatitis-inducing factor and/or plasma, according to an embodiment of the present invention.
Figure 3:
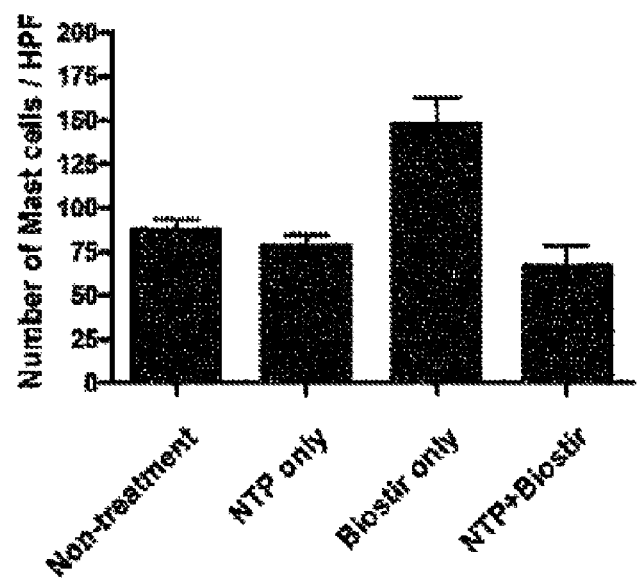
FIG. 3 is a graph showing EPX staining results of skin tissues of NC/Nga mice treated with an atopic dermatitis-inducing factor and/or plasma, according to an embodiment of the present invention.

The skin tissue of each mouse was obtained after the last treatment day for histological analysis. The obtained dorsal skin tissue was fixed in 4% paraformaldehyde for 24 hours, paraffin-embedded and cut to a thickness of 4.5 μm, and the morphology of the skin tissue was observed by hematoxylin and eosin (H & E) staining, the infiltration of mast cells into the skin tissue was examined by toluidine blue staining, and the influx of eosinophils into the tissue was observed by eosinophil peroxidase (EPX) antibody (Santa Cruz Biotechnology) staining. The results thereof were quantified and shown in FIGS. 1 to 3.

As a result of the experiment, it was confirmed that the epidermal morphology was not significantly different in the plasma control as compared with the negative control, but, in the positive control, the epidermis became very thick and the influx of mast cell or eosinophils into the tissue was significantly increased. In contrast, it was confirmed that the thickness of the epidermis was significantly decreased in the plasma experimental group as compared to the positive control, and the influx of mast cells or eosinophils into the tissue was maintained at a low level as compared to that of the negative control. This means that the plasma treatment can remarkably alleviate the symptoms of atopic dermatitis.

Example 1-2. Confirmation of Treatment Effect of Plasma-Treated Liquid Material on Atopic Dermatitis To confirm the treatment effect of plasma-treated liquid material on atopic dermatitis, experiments were conducted using a human keratinocyte cell line (HaCaT) and mast cells. HaCaT cells were obtained from the Korean Cell Line Bank and mast cells were obtained by culturing bone marrow cells of C57BL/6 mice in an RPMI 1640 medium supplemented with mIL-3 (10 ng/ml) and mSCF (50 ng/ml) at 37° C. and 5% $CO_2$ for 8 weeks, and then selecting the degree of differentiation of the cells by flow cytometry. plasma-treated liquid material was produced by irradiating a culture medium (RPMI 1640 or DMEM) with the plasma generated under the conditions of Example 1-1, for 60 seconds per ml.

Figure 4:
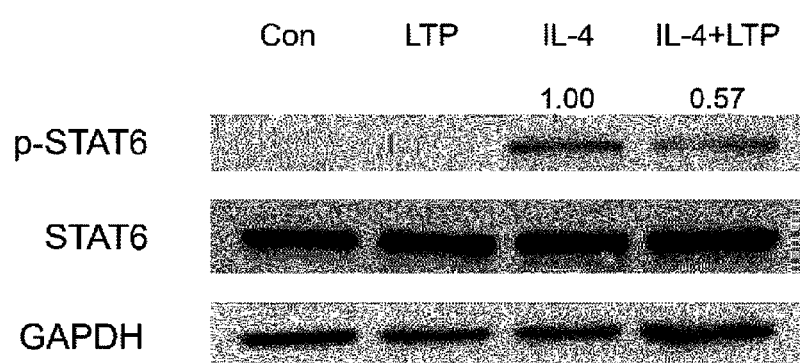
FIG. 4 is a graph showing the results of confirming an expression amount of p-STAT6 in HaCaT cells stimulated with IL-4 and treated with plasma-treated liquid material, according to an embodiment of the present invention.

First, the HaCaT cells were cultured after medium exchange with the culture medium treated with the plasma-treated liquid material, and after 1 hour of culturing, the HaCaT cells were stimulated with 30 ng/ml of interleukin-4 (IL-4), the cells were obtained after 15 minutes, and protein expression amounts of p-STAT6 (Abcam) and STAT6 (Cell Signaling Technology) were confirmed by western blotting. IL-4 is a hypersensitive activity factor and is known to promote inflammatory cytokines. As an experimental result, phosphorylation of a transcriptional activator (p-STAT6) was significantly reduced in the group treated with IL-4 and plasma-treated liquid material (LTP), as compared with the group treated only with IL-4. This means that the plasma-treated liquid material treatment can remarkably alleviate immune hypersensitivity reactions. The results thereof are shown in FIG. 4.

Next, after pre-treatment with plasma-treated liquid material for 1 hour, the mast cells were stimulated with 50 nM protease kinase C activator (PMA) capable of activating mast cells and 1 mM calcimycin (A23187), and further incubated for 6 hours, and qPCR was used to confirm the gene expression amounts of interleukin-6 (IL-6) and TNF-α. The qPCR was carried out by the same method as that used in Example 1-1. As a result of the experiment, both IL-6 and TNF-α showed a significant decrease in gene expression amount in the group treated with the inflammatory inducers and the plasma-treated liquid material (LTP), as compared with the group treated only with PMA/A23187. The results thereof are shown in FIGS. 5 and 6.

Lastly, the mast cells were pre-treated with a culture medium treated with plasma-treated liquid material for 1 hour, and then stimulated with a mast cell activating factor in the same manner as described above, and then further cultured for 30 minutes, and the activity of NF-kB was confirmed by western blotting. As a result of the experiment, the phosphorylation of NF-kB (p-NF-kB) was significantly reduced in the group treated with the inflammatory inducers and the plasma-treated liquid material (LTP), as compared to the group treated only with the inflammatory inducers. The results thereof are shown in FIG. 7.

Example 1-3. Comparison Between Effects of Plasma Direct Treatment and Plasma-Treated Liquid Material Treatment on Atopic Dermatitis The effect of the plasma-treated liquid material of the present invention on cells was compared with that of plasma direct treatment on cells. The plasma direct treatment was performed using the same plasma generator as that used in the production of the plasma-treated liquid material, wherein plasma was generated under the same conditions, and a culture dish where epidermal cells were cultured was directly exposed to plasma.

As a result of comparing the cells directly treated with the plasma-treated liquid material or plasma, it was analyzed that surfaces of the cells directly treated with plasma were dried. When considering that moisturizing is very important in atopy, it is determined that the usefulness of plasma-treated liquid material that may be provided in the form of a liquid material such as a moisturizing agent is significant.

Example 2. Confirmation of Psoriasis Treatment Effect of Plasma-Treated Liquid Material

Example 2-1. Confirmation of Psoriasis Treatment Effect of Non-Thermal Atmospheric Pressure Plasma (NTP)

Example 2-1-1. Psoriasis Treatment Effect of Non-Thermal Atmospheric Pressure Plasma (NTP) in Animal Model To verify the therapeutic effect of non-thermal plasma on psoriasis treatment, an animal model with psoriasis induced by applying imiquimod (IMQ) on the dorsal skin of each of hair-removed C57/BL6 mice was used. The dorsal hairs of 8-week-old C57/BL6 mice were removed, and then 62.5 mg/day of an IMQ cream (Sigma, U.S.A.) was applied on each mouse to induce psoriasis-like skin, and on day 3 and day 4, each mouse was treated with non-thermal plasma for 60 seconds at a distance of 2 cm from the epidermis of each mouse, using a plasma generator supplied with a voltage of 15 kV and a frequency of 15 kHz and using nitrogen gas as a carrier gas, and the mice were then sacrificed on day 5, followed by analysis of the skin tissue by immunohistochemical staining. A time frame for the imiquimod and plasma treatment is illustrated in FIG. 8.

Figure 9:
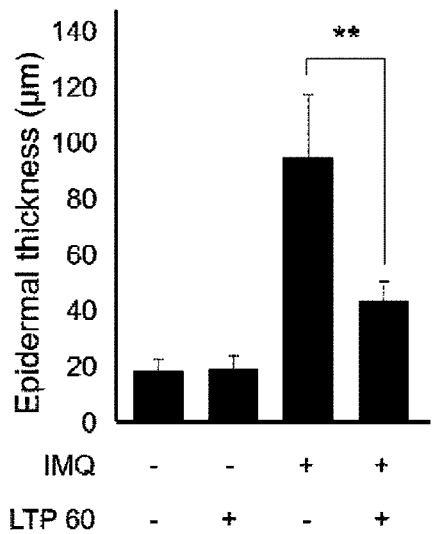
FIG. 9 is a graph showing changes in stratum corneum formation of the skin of mice treated with IMQ and/or NTP, according to an embodiment of the present invention.
Figure 10:
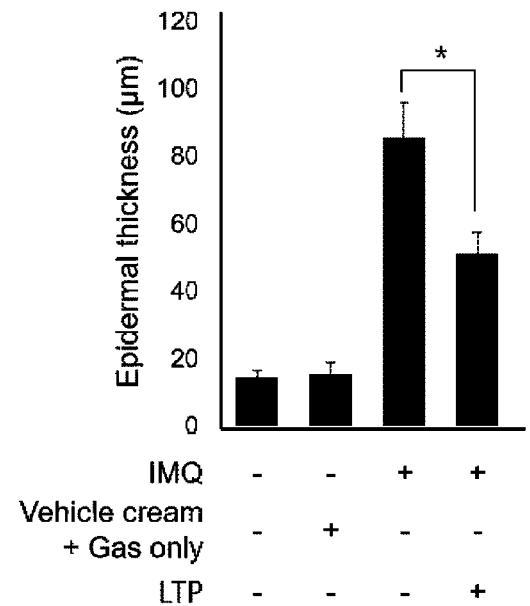
FIG. 10 is a graph showing that an IMQ vehicle cream and/or nitrogen gas did not significantly affect the stratum corneum formation of mouse skin, according to an embodiment of the present invention.
Figure 11A:
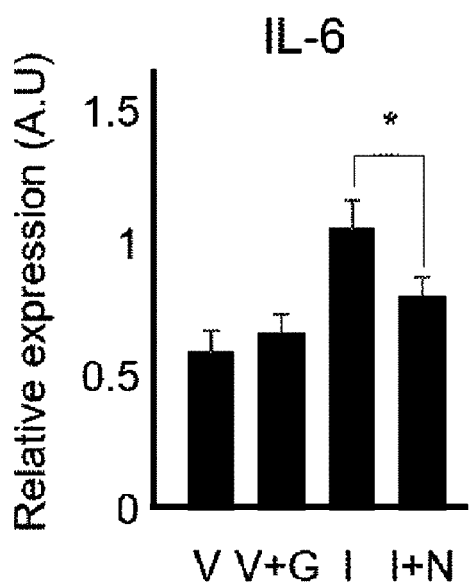
FIGS. 11A to 11E are graphs showing that NTP treatment did not significantly affect the inflammatory response factors of mouse skins, according to one embodiment of the present invention.
Figure 11B:
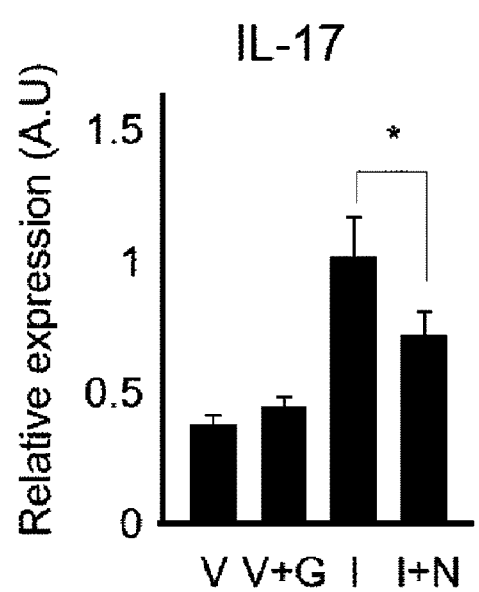
Figure 11C:
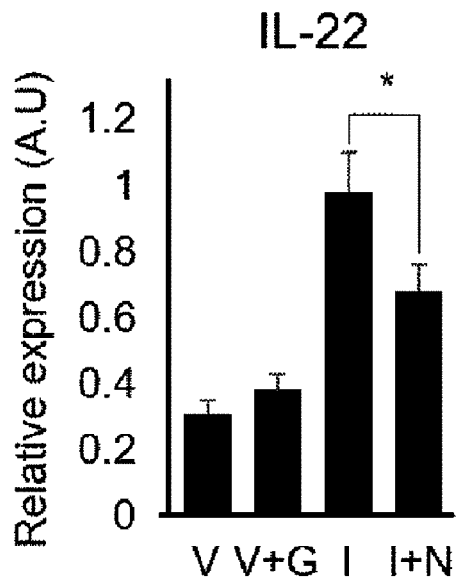
Figure 11D:
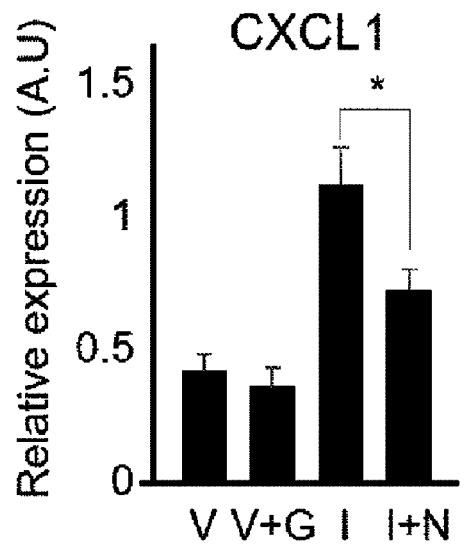
Figure 11E:
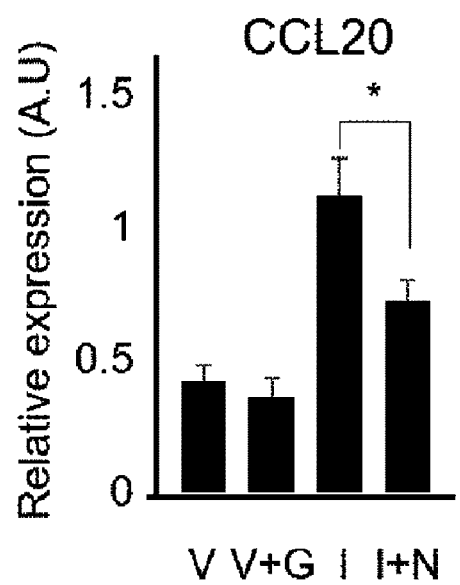
Figure 13A:
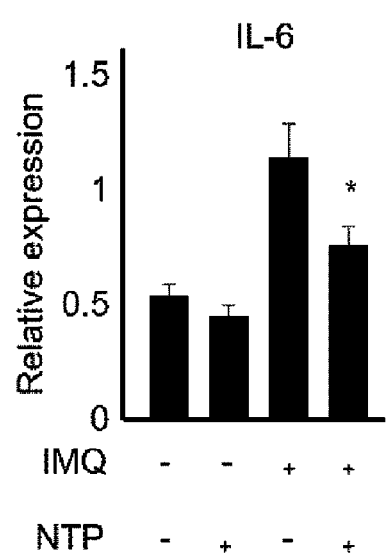
FIGS. 13A to 13E are graphs showing changes in the expression amounts of inflammatory response factors (IL-6, IL-17, IL-22, CXCL1, and CCL20) by IMQ stimulation and NTP treatment, according to an embodiment of the present.
Figure 13B:
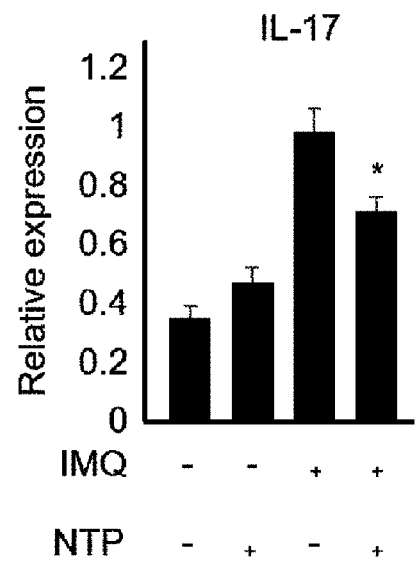
Figure 13C:
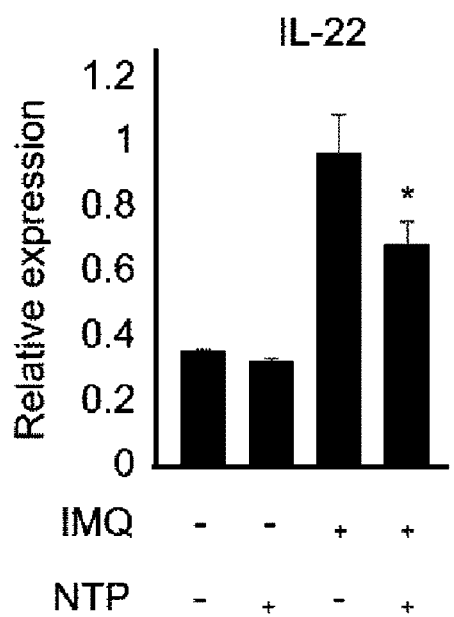
Figure 13D:
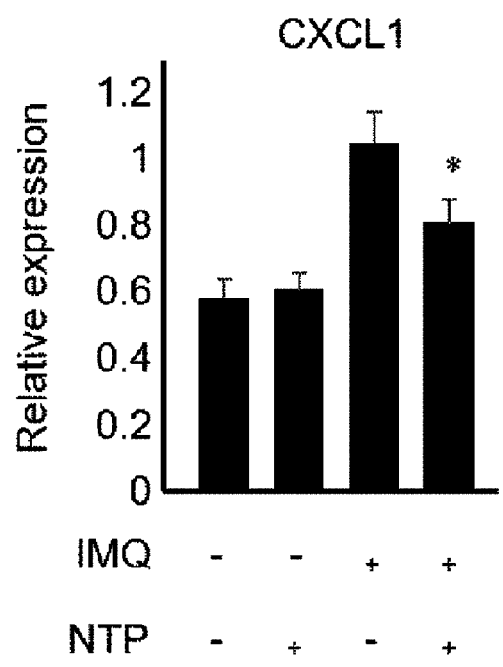
Figure 13E:
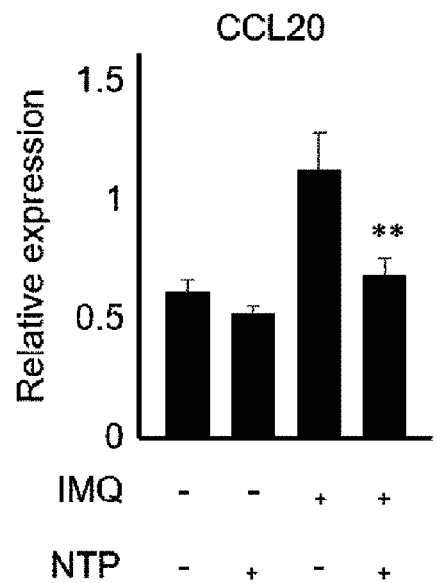

Experimental results showed that the thickness of the stratum corneum was significantly increased in IMQ-treated mice, but the mice treated with IMQ and NTP showed a 50% or more reduction in the thickness of the stratum corneum, as compared to the IMQ-treated mice. The results thereof are illustrated in FIG. 9. An experiment proving that the above result is an effect of plasma is shown in FIG. 10. Plasma treatment on normal mouse skin did not affect skin tissue, and mice treated with only a vehicle cream of IMQ or mice treated with the vehicle cream and nitrogen gas did not develop skin inflammation. In addition, the result that plasma treatment did not induce side effects in normal skin tissue was confirmed by a comparison in expression amount between various inflammatory response factors (IL-6, IL-17, IL-22, CXCL1, and CCL20). The results thereof are illustrated in FIGS. 11A to 11E.

Example 2-1-2. Inhibition of Immune Cell Infiltration in Animal Model by Non-Thermal Atmospheric Pressure Plasma (NTP)

To confirm whether non-thermal plasma can inhibit immune cell infiltration in psoriasis-like skin inflammation induced by IMQ, single cell suspensions of the skin of mice were analyzed by flow cytometry (FACS), and the results thereof are shown in FIGS. 12A to 12D. The experimental results showed that the infiltration of CD4+T cells, CD11c+ cells, CD11b+ cells, and Gr-1+ cells was increased in IMQ-treated mouse skin, and immunocytic infiltration was suppressed in IMQ- and plasma-treated skin.

In addition, the expression amounts of the inflammatory response factors (IL-6, IL-17, IL-22, CXCL1, and CCL20) were also compared, and the results thereof are illustrated in FIGS. 13A to 13E. From the results of Example 2-1-1, it was confirmed that the plasma treatment on normal skin did not cause inflammatory reaction factor changes. However, as a result of the experiment, the expression of cytokines and chemokines increased more than twofold in the IMQ-treated skin as compared to the negative control or the group treated only with plasma, whereas the expression of cytokines and chemokines was significantly reduced in the IMQ- and plasma-treated skin.

From the results of FIGS. 12 and 13, it can be seen that the non-thermal plasma treatment can effectively alleviate psoriasis-like skin inflammation through inhibition of the gene expression of inflammatory cytokines and chemokines.

Example 2-1-3. Inhibition of Th17 Cell Differentiation in Animal Model by Non-Thermal Atmospheric Pressure Plasma (NTP)

It was observed whether the non-thermal plasma according to the present invention inhibited the differentiation of Th17 cells induced by IMQ in drainage lymph nodes of C57/BL6 mice. Th17 cells are known to be important for the pathogenesis of psoriasis. The degree of differentiation of Th17 cells was analyzed by flow cytometry (FACS) in the same manner as in Example 2-1-1.

Figure 14:
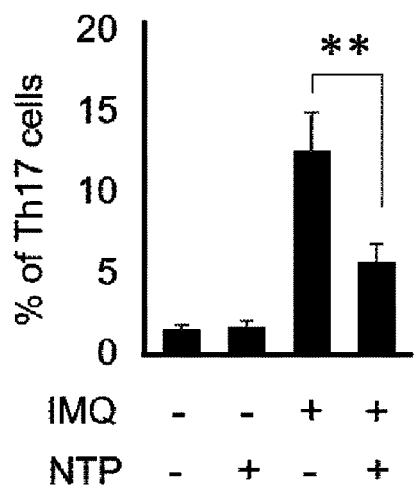
FIG. 14 is a graph showing the degree of suppression of Th17 cell differentiation by IMQ stimulation and NTP treatment, according to an embodiment of the present invention.

The experimental results showed that, when mice were treated with IMQ, the number of Th17 cells was increased in drainage lymph nodes, but this was effectively inhibited by plasma treatment. The result thereof is shown in FIG. 14.

Example 2-2. Confirmation of Effect of Plasma-Treated Liquid Material (LTP) on Psoriasis Treatment

Example 2-2-1. Production of Plasma-Treated Liquid Material (LTP)

Figure 15A:
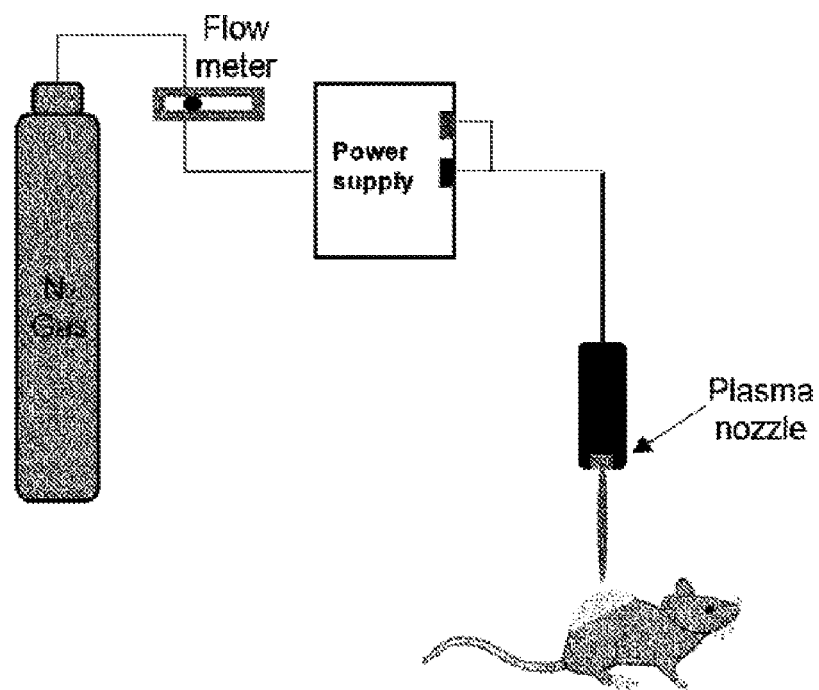
FIGS. 15A and 15B are schematic diagrams illustrating a comparison between a method of producing LTP and a method of producing NTP, according to an embodiment of the present invention.
Figure 15B:
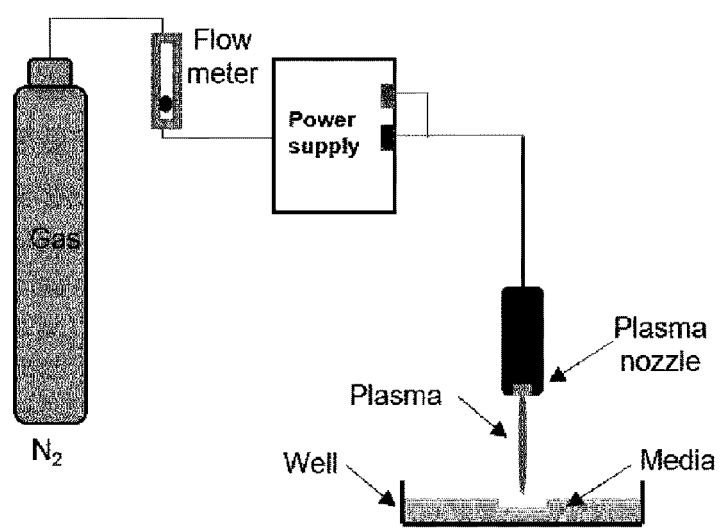

Plasma-treated liquid material was produced by irradiating a culture medium (RPMI 1640 or DMEM) with the plasma generated under the conditions of Example 2-1-1 for 0 second (No LTP), 30 seconds (LTP 30), or 60 seconds (LTP 60), per ml. Schematic diagrams of treatment with non-thermal atmospheric pressure plasma (NTP) and plasma-treated liquid material (LTP) of Example 2-1 are illustrated in FIGS. 15A and 15B.

Example 2-2-2. Inhibition of Th17 Cell Differentiation by Plasma-Treated Liquid Material (LTP)

Figure 16:
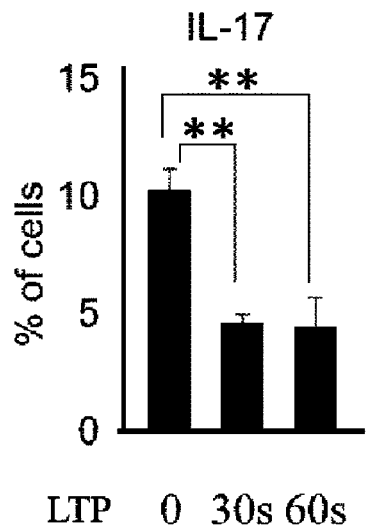
FIG. 16 is a graph showing a degree of inhibition of Th17 cell differentiation upon treatment with No LTP, LTP 30, or LTP 60, according to an embodiment of the present invention.

To observe whether the differentiation of Th17 cells was inhibited by plasma-treated liquid material as in the non-thermal atmospheric pressure plasma of Example 2-1, CD4+T cells of normal C57/BL6 mice were isolated and the isolated cells were differentiated into Th17 cells in an RPMI1640 culture solution including 10 ng/ml of anti-CD3, 5 ng/ml of anti-CD28, 10 ng/ml of IL-6, 5 ng/ml of TGF-β, an IFN-γ antibody, and an IL-4 antibody. At this time, No LTP, LTP 30, or LTP 60 was used as the culture solution. The degree of differentiation of Th17 cells in each culture solution was observed through flow cytometry (FACS), and the results thereof are shown in FIG. 16. As a result of the experiment, it was confirmed that, while the differentiation of IL-17-expressing Th17 was exhibited in the culture solution not treated with plasma (No LTP), the differentiation of Th17 was significantly inhibited in the culture solutions treated with plasma (LTP30 and LTP60).

Figure 17:
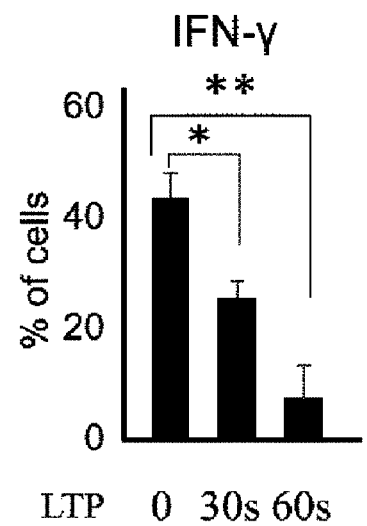
FIG. 17 is a graph showing a degree of inhibition of Th1 cell differentiation upon treatment with No LTP, LTP 30, or LTP 60, according to an embodiment of the present invention.

Example 2-2-3. Effect of Plasma-Treated Liquid Material (LTP) on Inhibiting the Differentiation of Th1 Cells To observe whether the differentiation of Th1 cells was inhibited by plasma-treated liquid material, the CD4+ T cells isolated from mice in Example 2-2-2 were differentiated into Th1 cells in an RPMI1640 culture solution containing 10 ng/ml of anti-CD3, 5 ng/ml of anti-CD28, and 10 ng/ml of IL-12. At this time, No LTP, LTP 30, or LTP 60 was used as the culture solution. The degree of differentiation of Th1 cells in each culture solution was observed through flow cytometry (FACS), and the results thereof are shown in FIG. 17. As a result of the experiment, Th1 cell differentiation was induced in the culture solution not treated with plasma (No LTP), but the Th1 cell differentiation was significantly inhibited in the culture solutions treated with plasma, i.e., LTP 30 and LTP 60. In particular, it was confirmed that almost no differentiation into Th1 cells occurred in the culture solution LTP 60.

Figure 18:
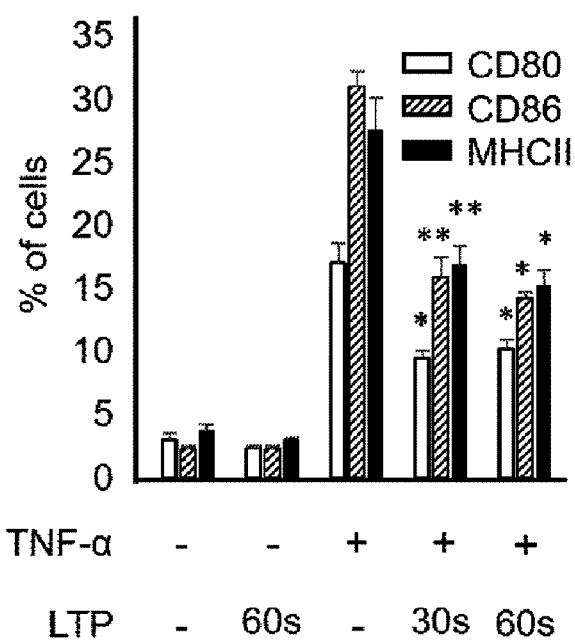
FIG. 18 is a graph showing the expression of CD80, CD86, and MHC II as a degree of inhibition of BMDC activity by LTP treatment, according to an embodiment of the present invention.
Figure 19A:
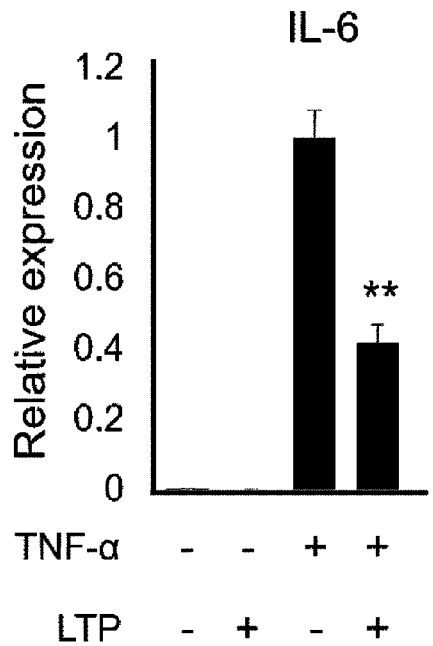
FIGS. 19A to 19E are graphs showing decreases in the expression of inflammatory cytokines by LTP treatment in BMDC treated with TNF-α, according to an embodiment of the present invention.
Figure 19B:
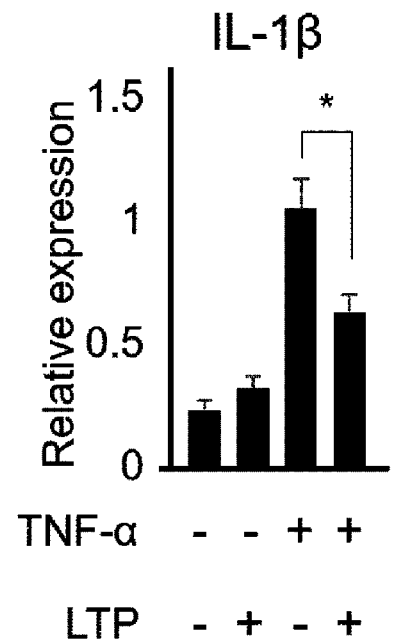
Figure 19C:
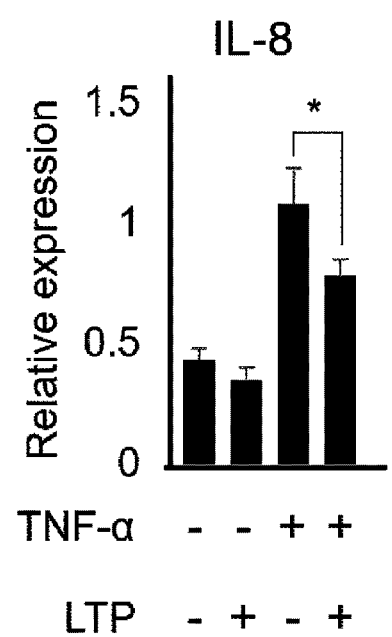
Figure 19D:
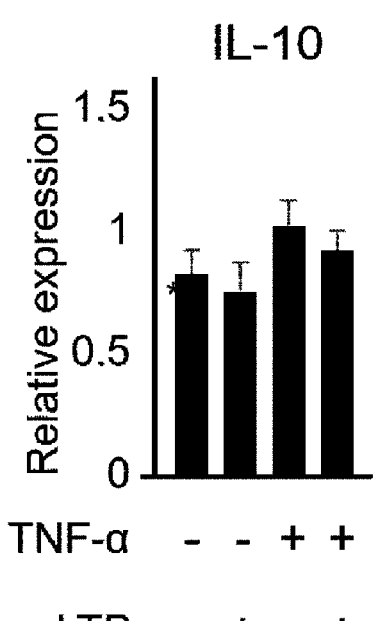
Figure 19E:
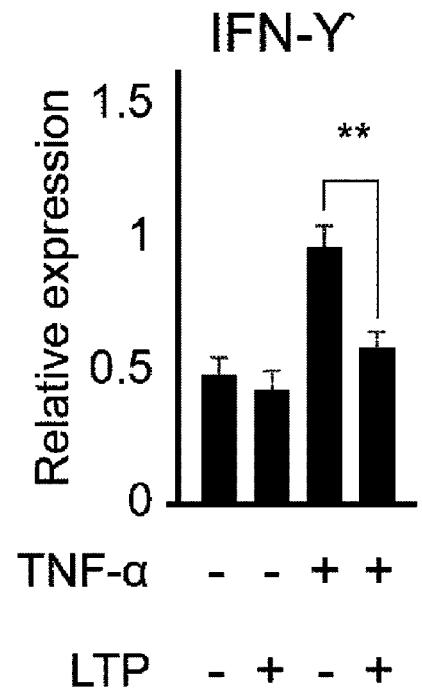
Figure 20A:
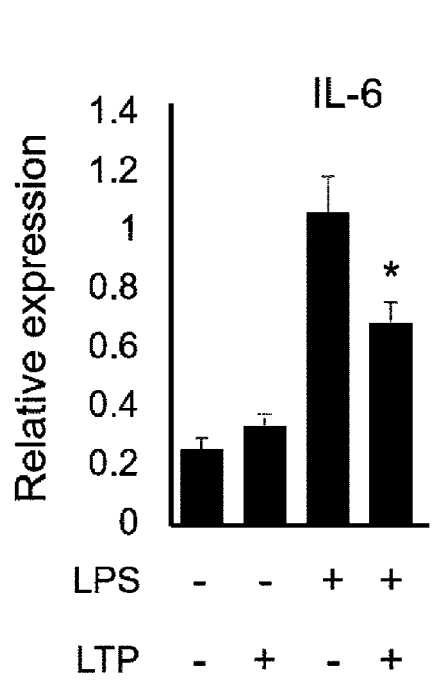
FIGS. 20A to 20E are graphs showing decreases in the expression of inflammatory cytokines by LTP treatment in BMDC treated with lipopolysaccharides (LPS), according to an embodiment of the present invention.
Figure 20B:
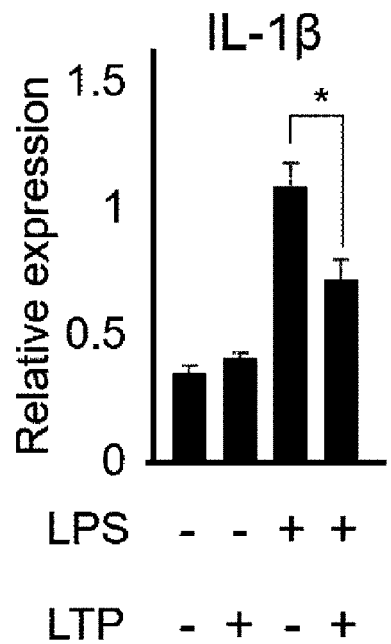
Figure 20C:
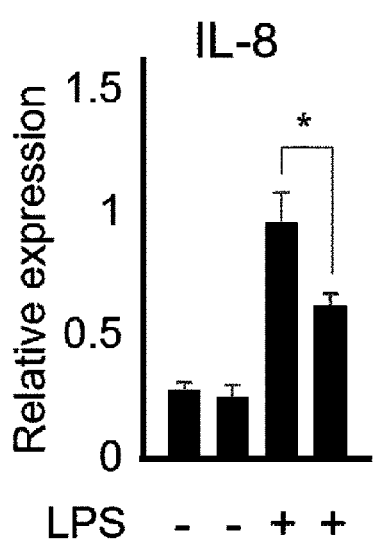
Figure 20D:
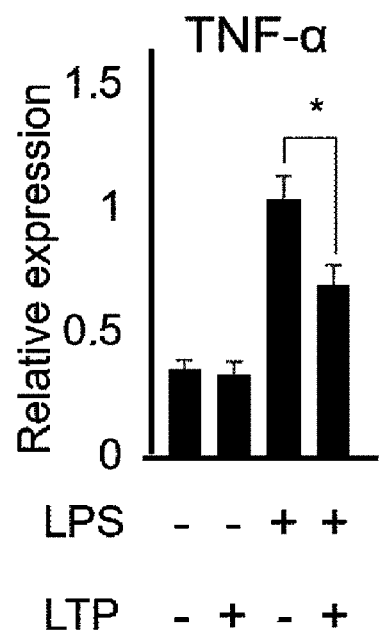
Figure 20E:
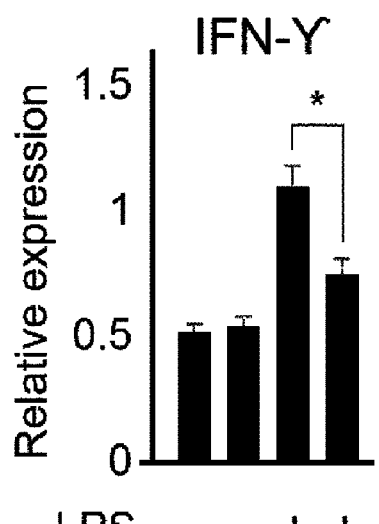
Figure 21A:
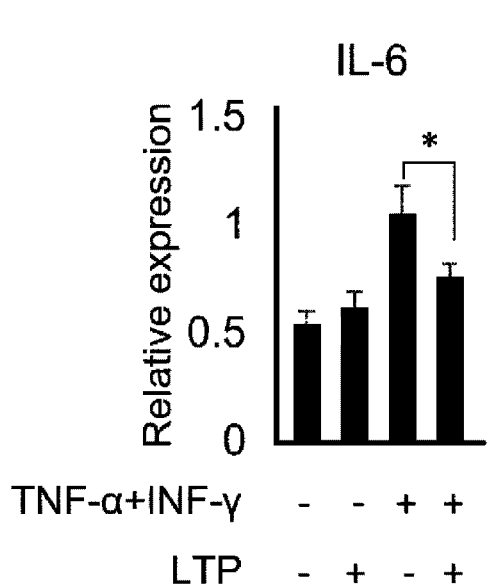
FIGS. 21A to 21E are graphs showing changes in gene expression of interleukins and cytokines by LTP treatment in HaCaT cells activated with TNF-α and IFN-γ, according to an embodiment of the present invention.
Figure 21B:
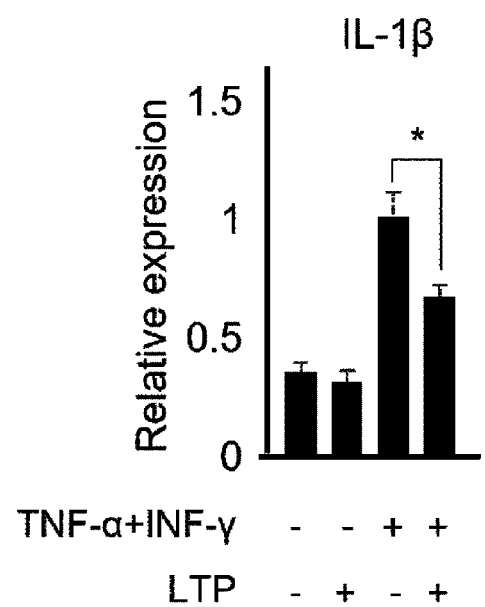
Figure 21C:
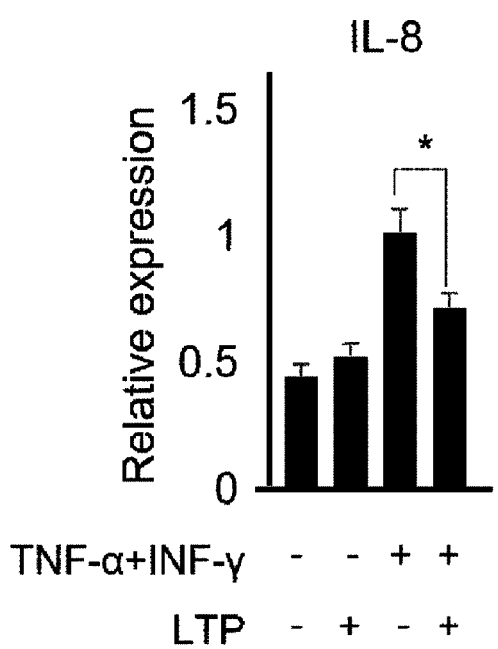
Figure 21D:
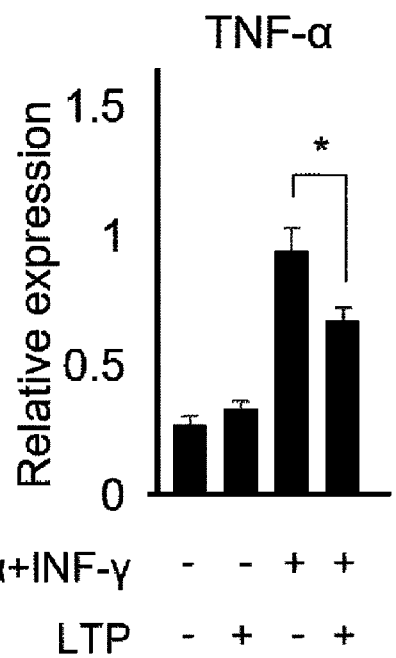
Figure 21E:
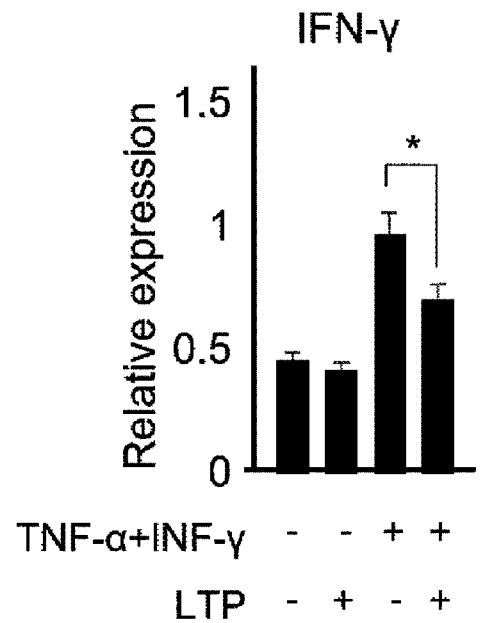
Figure 22A:
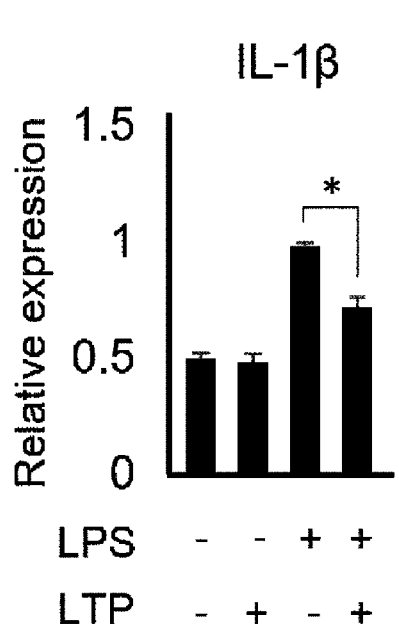
FIGS. 22A to 22G are graphs showing changes in gene expression of interleukins and cytokines by LTP treatment in LPS-stimulated HaCaT cells, according to an embodiment of the present invention.
Figure 22B:
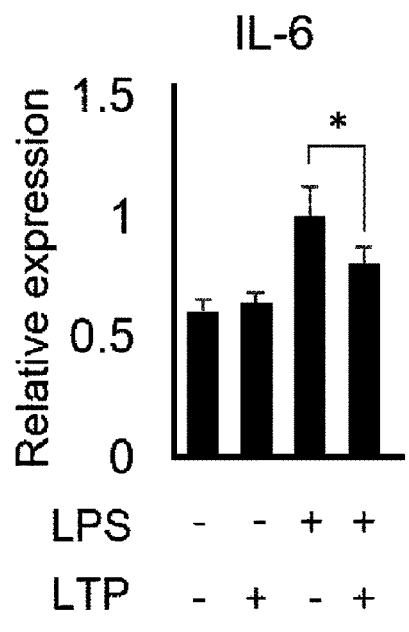
Figure 22C:
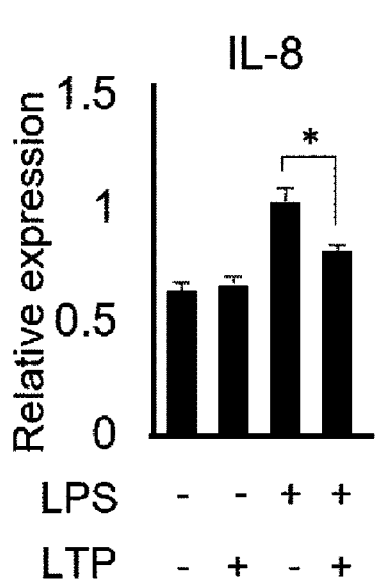
Figure 22D:
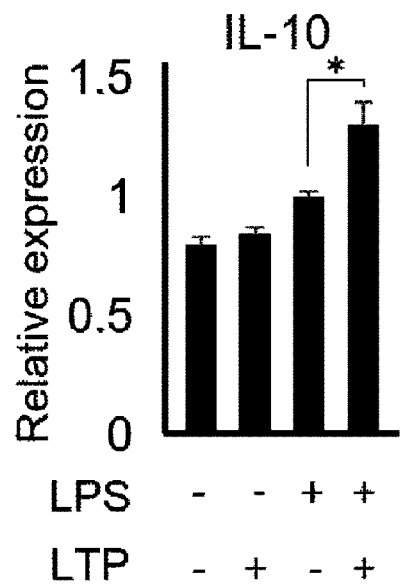
Figure 22E:
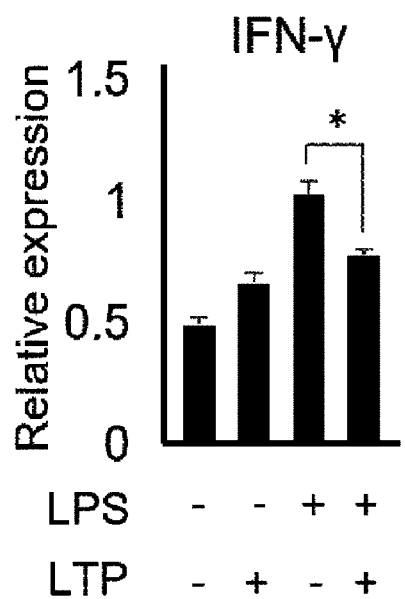
Figure 22F:
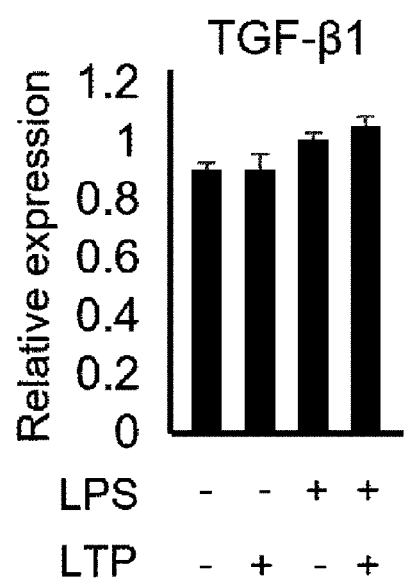
Figure 22G:
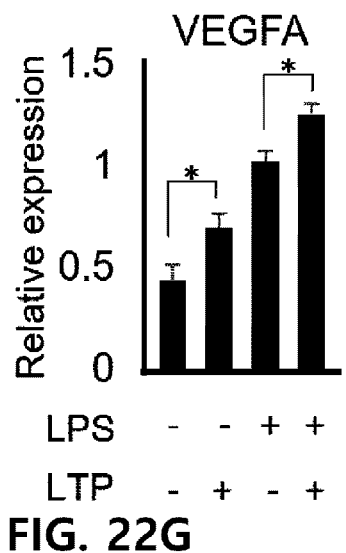

Example 2-2-4. Effect of Plasma-Treated Liquid Material (LTP) on Inhibition of BMDC Cell Activity To observe whether the activity of bone marrow-derived dendritic cells (BMDCs) was inhibited by the plasma-treated liquid material according to the present invention, bone marrow cells of normal C57/BL6 mice were isolated, and the isolated bone marrow cells were activated with TNF-α (20 μg/ml) in the same culture solution as that of Example 2-2-2, and then the expression of CD80 and CD86, which are activation marker factors of dendritic cells, and MHC II was measured. TNF-α is known to be involved in the pathogenesis of psoriasis. As a result of the experiment, TNF-αstimulation enhanced the expression of CD80, CD86, and MHCII in BMDCs, while the expression of CD80, CD86, and MHC II and TNF-a production were significantly reduced in the culture solutions treated with plasma, i.e., LTP 30 and LTP 60. The results thereof are shown in FIG. 18.

In addition, the expression of inflammatory cytokines was confirmed in BMDCs treated with TNF-α or lipopolysaccharides (LPS). Among the interleukins and cytokines used in the present invention, primer sets of mouse IL-6, IL-17, TNF-α, CXCL1, CCL20, PD-L1, and GAPDH were purchased and used (Qiagen, Hilden, Germany), and primer sets of human IL-1β, IL-8, IL-10, IFN-γ, and TGF-β1 were synthesized to have sequences listed in Table 2 below. GAPDH was used as a negative control.

TABLE 2

| | | |
|---|---|---|
| hIL-1β | Forward | 5'ACAGATGAAGTGCTCCTTCCA3' |
| | Reverse | 5'GTCGGAGATTCGTAGCTGGAT3' |
| hIL-8 | Forward | 5'ATGACTTCCAAGCTGGCCGTGGCT3' |
| | Reverse | 5'TCTCAGCCCTCTTCAAAAACTTCT3' |
| hIL-10 | Forward | 5'CATCGATTTCTTCCCTGTGAA3' |
| | Reverse | 5'TCTTGGAGCTTATT AAAGGCATTC3' |
| hIFN-γ | Forward | 5'CTAATTATTCGGTAACTGACTTGA3' |
| | Reverse | 5'ACAGTTCAGCCATCACTTGGA3' |
| hTGF-β1 | Forward | 5'CCCAGCATCTGCAAAGCTC3' |
| | Reverse | 5'GTCAATGTACAGCTGCCGCA3' |

The experimental results showed that the expression of inflammatory cytokines was increased in BMDCs treated with TNF-α or lipopolysaccharides (LPS), and the expression of inflammatory cytokines was decreased by plasma-treated liquid material. These results suggest that plasma may negatively regulate DC activation that inhibits the activation and differentiation of T cells. The results thereof are shown in FIGS. 19A to 19E and FIGS. 20A to 20E.

Example 2-2-5. Anti-Inflammatory Effect of Plasma-Treated Liquid Material (LTP) on Activated HaCaT (Epithelial Cell) Cell To confirm the anti-inflammatory effect of plasma-treated liquid material on psoriasis-like skin, the expression of inflammatory factors in HaCaT cells was analyzed. To this end, first, HaCaT cells were activated with TNF-α and IFN-γ, treated with plasma-treated liquid material, and gene expression of cytokines involved in psoriasis was measured by real-time PCR. The results thereof are shown in FIGS. 21A to 21E. The experimental results showed that plasma-treated liquid material had an anti-inflammatory effect on HaCaT cells stimulated by TNF-α and IFN-γ.

The effect of plasma-treated liquid material on the gene expression of IL-1β, IL-6, IL-8, IL-10, IFN-γ, TGF-β1, and VEGFA in LPS-stimulated HaCaT cells was also confirmed. The experimental results showed that expression amounts of IL-1β, IL-6, IL-8, and IFN-γ increased by LPS stimulation were reduced by treatment with plasma-treated liquid material, expression amounts of IL-10 and VEGFA were further increased by treatment with plasma-treated liquid material, and the case of TGF-β1 did not show any significant change. The results thereof are shown in FIGS. 22A to 22G.

Figure 23A:
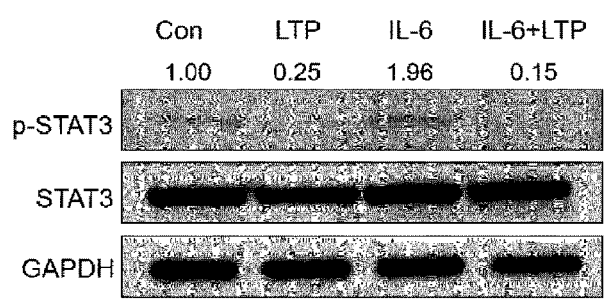
FIGS. 23A and 23B are graphs showing changes in STAT3 activation (pSTAT3) by LTP treatment in HaCaT cells stimulated with IL-6, according to an embodiment of the present invention.
Figure 23B:
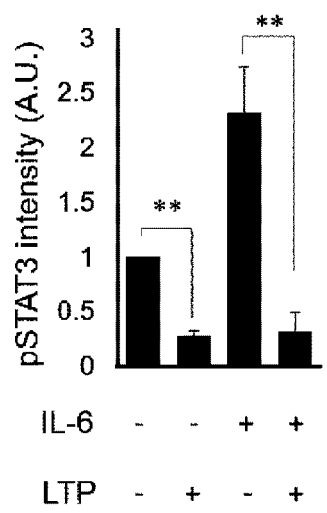

In addition, it was confirmed whether plasma-treated liquid material affected STAT3 activation in HaCaT cells. STAT3 activation is known to play an important role in Th17 cell differentiation and psoriasis pathogenesis. The results thereof are shown in FIGS. 23A and 23B. The experimental results showed that plasma-treated liquid material treatment inhibited STAT3 activation (pSTAT3) in IL-6 stimulated HaCaT cells. These results suggest that plasma-treated liquid material may induce the inhibition of psoriasis in mice by inhibiting the STAT3 signaling pathway.

Example 2-2-6. Confirmation of Increase in PD-L1 Expression in Activated HaCaT and BMDC Cells by Plasma-Treated Liquid Material (LTP)

Figure 24A:
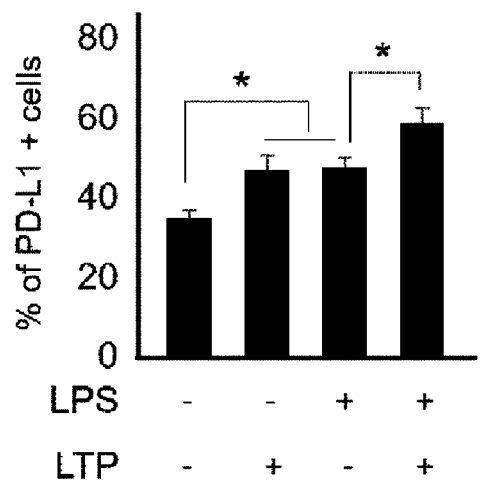
FIGS. 24A to 24C are graphs showing changes in PD-L1 expression by LTP treatment in HaCaT cells stimulated with TNF-α, IFN-γ, or LPS, according to an embodiment of the present invention.
Figure 24B:
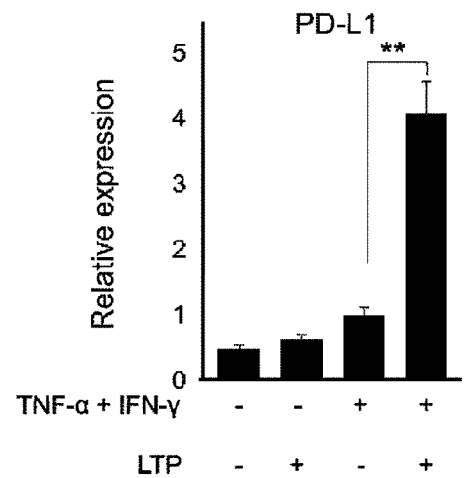
Figure 24C:
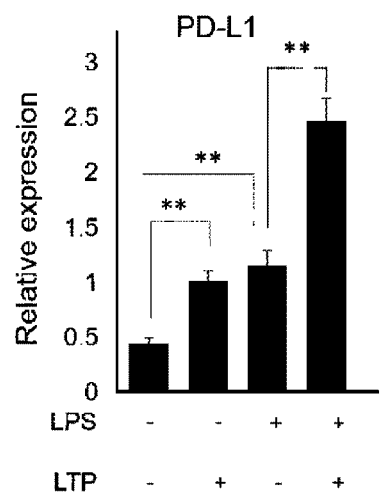

It was confirmed whether the expression of PD-L1 was increased in HaCaT and BMDC cells activated by the plasma-treated liquid material according to the present invention, and the results thereof are shown in FIGS. 24A to 24C. It has been reported that PD-L1 expression in DC inhibits T cell activation through PD-1/PD-L1 binding. Thus, it has been proposed that overexpression or high expression of PD-L1 can induce T cell inactivation and help in the treatment of autoimmune diseases in which CD4+T cells are abnormally activated. Recently, it has been reported that administration of recombinant PD-L1 has improved skin inflammation induced by IMQ in mice.

The experimental results showed that plasma-treated liquid material treatment induces PD-L1 expression in HaCaT cells. In addition, the level of PD-L1 RNA was increased in TNF-α/IFN-γ-stimulated or LPS-stimulated HaCaT cells, and plasma-treated liquid material treatment in stimulated cells further enhanced PD-L1 expression. These results suggest that plasma-treated liquid material treatment may alleviate psoriasis-like skin inflammation through modulation of PD-L1 gene expression.

Examples 2-3. Comparison Between Psoriasis Treatment Effects of Non-Thermal Atmospheric Pressure Plasma (NTP) and Plasma-Treated Liquid Material (LTP)

The effect of the plasma-treated liquid material of the present invention on cells was compared with that of plasma direct treatment on cells. The plasma direct treatment was performed using the same plasma generator as that used in the production of the plasma-treated liquid material, wherein plasma was generated under the same conditions, and a culture dish where the TNF-α/IFN-γ-stimulated HaCaT cells were cultured was directly exposed to plasma.

As a result of comparing the cells directly treated with the plasma-treated liquid material or plasma, it was analyzed that surfaces of the cells directly treated with plasma were dried. When considering that moisturizing is very important in atopy, it is determined that the usefulness of plasma-treated liquid material that may be provided in the form of a liquid material such as a moisturizing agent is significant.

From the results of Example 1, it can be seen that the plasma-treated liquid material of the present invention is remarkably effective in alleviating the symptoms of atopic dermatitis. From the results of Example 2, it can be seen that the plasma-treated liquid material of the present invention is remarkably effective in preventing and treating skin inflammatory diseases including psoriasis.

INDUSTRIAL APPLICABILITY

Plasma-treated liquid material of the present invention has a significant effect of inhibiting immune hypersensitivity reactions and has an effect of inhibiting the induction and progress of psoriasis, and thus is expected to be greatly utilized in preventing and treating immune hypersensitivity reactions including atopic dermatitis or psoriasis.

The invention claimed is:

1. A method comprising:
   (a) filling a plasma generator with a carrier gas;
   (b) supplying a voltage of 1 kV to 13 kV and a frequency of 15 kHz to 30 kHz to the plasma generator to generate plasma;
   (c) treating a liquid material with the generated plasma to produce a plasma-conditioned liquid material; and
   (d) administering the plasma-conditioned liquid material by apply the plasma-conditioned liquid material to the skin or injecting the plasma-conditioned liquid material subcutaneously or intradermally to prevent or treat an allergic disease.

2. The method of claim 1, wherein, in process (a), the carrier gas comprises any one or more selected from the group consisting of nitrogen, helium, argon, and oxygen.

3. The method of claim 1, wherein the treating of process (c) is performed at a distance of 0.1 cm to 15 cm from a surface of the liquid material for 5 minutes to 30 minutes.

4. The method of claim 1, wherein the liquid material of process (c) is water, saline, a buffer, or a medium.

5. The method of claim 1, wherein the allergic disease is allergic rhinitis, asthma, a food allergy, or atopic dermatitis.

6. The method of claim 1 wherein the administrating step includes forming a pharmaceutical composition comprising, as an active ingredient, plasma-treated liquid material and applying the pharmaceutical composition to the skin or injecting the plasma-conditioned liquid material subcutaneously or intradermally.

7. The method of claim 6, wherein the pharmaceutical product includes a protein.

8. The method of claim 7 wherein the pharmaceutical product includes an excipient, a carrier, or a diluent.

9. A method comprising:
   (a) filling a plasma generator with a carrier gas;
   (b) supplying a voltage of 5 kV to 20 kV and a frequency of 10 kHz to 30 kHz to the plasma generator to generate plasma;
   (c) treating a liquid material with the generated plasma to produce a plasma-conditioned liquid; and
   (d) administering the plasma-conditioned liquid material by applying the plasma-conditioned liquid material to the skin or injecting the plasma-conditioned liquid material subcutaneously or intradermally to prevent or treat a T-lymphocyte mediated skin disease.

10. The method of claim 9, wherein, in process (a), the carrier gas comprises any one or more selected from the group consisting of nitrogen, helium, argon, and oxygen.

11. The method of claim 9, wherein the treating of process (c) is performed at a distance of 0.1 cm to 15 cm from a surface of the liquid material for 5 minutes to 120 minutes.

12. The method of claim 9, wherein the liquid material of process (c) is water, saline, a buffer, or a medium.

13. The method of claim 9, wherein the T lymphocyte-mediated skin disease comprises any one or more selected from the group consisting of systemic lupus erythematosus, cutaneous lupus erythematosus, scleroderma, psoriasis, dermatomyositis, and chronic dermatitis.

14. The method of claim 9 wherein the administrating step includes forming a pharmaceutical composition comprising, as an active ingredient, the plasma conditioned liquid material; and applying the pharmaceutical composition to the skin or injecting the plasma-conditioned liquid material subcutaneously or intradermally.

15. The method of claim 14, wherein the pharmaceutical product includes a protein.

16. The method of claim 15 wherein the pharmaceutical product includes an excipient, a carrier, or a diluent.

\* \* \* \* \*